(12) United States Patent
Markovic

(10) Patent No.: US 9,387,244 B2
(45) Date of Patent: Jul. 12, 2016

(54) METHODS FOR REDUCING GLOBAL CHRONIC INFLAMMATION AND THE PRESENCE OF MELANOMA

(71) Applicant: Mayo Foundation for Medical Education and Research, Rochester, MN (US)

(72) Inventor: Svetomir N. Markovic, Rochester, MN (US)

(73) Assignee: Mayo Foundation for Medical Education and Research, Roschester, MN (US)

( * ) Notice: Subject to any disclaimer, the term of this patent is extended or adjusted under 35 U.S.C. 154(b) by 0 days.

(21) Appl. No.: 14/051,849

(22) Filed: Oct. 11, 2013

(65) Prior Publication Data

US 2014/0056909 A1 Feb. 27, 2014

Related U.S. Application Data

(63) Continuation of application No. 12/979,105, filed on Dec. 27, 2010, now abandoned, which is a continuation-in-part of application No. PCT/US2009/049511, filed on Jul. 2, 2009.

(60) Provisional application No. 61/078,203, filed on Jul. 3, 2008.

(51) Int. Cl.
| | |
|---|---|
| *A61K 39/00* | (2006.01) |
| *A61K 38/00* | (2006.01) |
| *A61K 51/10* | (2006.01) |
| *A61K 39/395* | (2006.01) |
| *A61K 31/337* | (2006.01) |
| *A61K 31/4188* | (2006.01) |
| *A61K 31/555* | (2006.01) |
| *A61K 31/675* | (2006.01) |
| *A61K 45/06* | (2006.01) |
| *A61K 31/56* | (2006.01) |

(52) U.S. Cl.
CPC ......... *A61K 39/39533* (2013.01); *A61K 31/337* (2013.01); *A61K 31/4188* (2013.01); *A61K 31/555* (2013.01); *A61K 31/56* (2013.01); *A61K 31/675* (2013.01); *A61K 39/0011* (2013.01); *A61K 45/06* (2013.01); *A61K 51/1069* (2013.01); *A61K 2039/545* (2013.01)

(58) Field of Classification Search
None
See application file for complete search history.

(56) References Cited

U.S. PATENT DOCUMENTS

| | | | |
|---|---|---|---|
| 4,350,687 | A | 9/1982 | Lipton et al. |
| 5,116,944 | A | 5/1992 | Sivam et al. |
| 5,216,130 | A | 6/1993 | Line et al. |
| 5,252,713 | A | 10/1993 | Morgan, Jr. et al. |
| 5,260,308 | A | 11/1993 | Poduslo et al. |
| 5,728,541 | A | 3/1998 | Kornblith |
| 5,736,137 | A | 4/1998 | Anderson et al. |
| 6,054,297 | A | 4/2000 | Carter et al. |
| 6,147,060 | A | 11/2000 | Zasloff et al. |
| 6,416,967 | B2 | 7/2002 | Kornblith |
| 6,537,579 | B1 | 3/2003 | Desai et al. |
| 6,933,129 | B1 | 8/2005 | Kornblith |
| 7,112,409 | B2 | 9/2006 | Blumenthal et al. |
| 7,678,552 | B2 | 3/2010 | Kornblith |
| 7,906,121 | B2 | 3/2011 | Chang et al. |
| 8,119,129 | B2 | 2/2012 | Jure-Kunkel et al. |
| 8,344,177 | B2 | 1/2013 | Neri et al. |
| 2002/0111362 | A1 | 8/2002 | Rubinfeld |
| 2004/0005318 | A1 | 1/2004 | Davis et al. |
| 2004/0077601 | A1 | 4/2004 | Adams et al. |
| 2005/0032699 | A1 | 2/2005 | Holash et al. |
| 2006/0165652 | A1 | 7/2006 | Dudley et al. |
| 2007/0020232 | A1 | 1/2007 | Rossignol et al. |
| 2009/0004118 | A1 | 1/2009 | Nie et al. |
| 2010/0047234 | A1 | 2/2010 | Markovic |
| 2010/0112077 | A1 | 5/2010 | Desai et al. |
| 2010/0172835 | A1 | 7/2010 | Ruoslahti et al. |
| 2011/0097340 | A1 | 4/2011 | Ramachandra et al. |
| 2011/0150902 | A1 | 6/2011 | Markovic |
| 2012/0315273 | A1 | 12/2012 | Markovic |
| 2014/0178486 | A1 | 6/2014 | Markovic |
| 2014/0302017 | A1 | 10/2014 | Markovic |

FOREIGN PATENT DOCUMENTS

| | | |
|---|---|---|
| EP | 1 913 947 | 4/2008 |
| JP | 2001-0072589 | 3/2001 |
| WO | WO 89/10398 | 11/1989 |
| WO | WO 99/51248 | 10/1999 |
| WO | WO 2004/096224 | 11/2004 |
| WO | WO 2008/057562 | 5/2008 |
| WO | WO 2008/112987 | 9/2008 |
| WO | WO 2009/043159 | 4/2009 |

(Continued)

OTHER PUBLICATIONS

Australian Office Action in Application No. 2008224929, issued Jun. 25, 2012, 3 pages.

(Continued)

*Primary Examiner* — Christine J Saoud
*Assistant Examiner* — Jegatheesan Seharaseyon
(74) *Attorney, Agent, or Firm* — Fish & Richardson P.C.

(57) ABSTRACT

This document relates to methods and materials involved in treating cancer (e.g., melanoma). For example, methods and materials involved in using an anti-chronic inflammation treatment (e.g., chemotherapy) in combination with a cancer treatment agent (e.g., a cancer vaccine) to treat cancer are provided.

6 Claims, 17 Drawing Sheets

(56) References Cited

FOREIGN PATENT DOCUMENTS

| WO | WO 2009/055343 | 4/2009 |
|---|---|---|
| WO | WO 2010/017216 | 2/2010 |
| WO | WO 2012/154861 | 11/2012 |

OTHER PUBLICATIONS

Australian Office Action in Application No. 2008224929, issued May 31, 2013, 3 pages.
European Office Action for Application No. 09774506.1, dated Nov. 13, 2012, 3 pages.
European Search Report for Application No. 09774506.1, dated Mar. 22, 2012, 12 pages.
European Search Report in Application No. 08743903.0 , dated Feb. 7, 2011, 8 pages.
International Preliminary Report on Patentability for Application No. PCT/US2009/049511, issued Jan. 5, 2011, 6 pages.
International Preliminary Report on Patentability for PCT/US2012/037137 mailed Nov. 21, 2013, 5 pages.
International Preliminary Report on Patentability in PCT/US2008/057025, dated Sep. 24, 2009, 6 pages.
International Search Report and Written Opinion for Application No. PCT/US2008/057025, mailed Jul. 1, 2008, 11 pages.
International Search Report and Written Opinion for Application No. PCT/US2009/049511, mailed Feb. 2, 2010, 8 pages.
International Search Report and Written Opinion of international application No. PCT/US2012/037137 mailed Sep. 28, 2012, 5 pages.
United States Office Action in U.S. Appl. No. 12/295,834, Jan. 27, 2012, 9 pages.
United States Office Action in U.S. Appl. No. 12/295,834, mailed Sep. 9, 2011, 7 pages.
United States Office Action in U.S. Appl. No. 13/591,847, mailed Sep. 19, 2012, 10 pages.
United States Office Action in U.S. Appl. No. 13/591,847, mailed Feb. 19, 2013, 14 pages.
United States Office Action in U.S. Appl. No. 13/591,847, mailed Dec. 19, 2013, 28 pages.
United States Office Action in U.S. Appl. No. 12/979,105, mailed Oct. 5, 2012, 16 pages.
United States Office Action in U.S. Appl. No. 12/979,105, mailed Apr. 11, 2013, 23 pages.
Agarwal et al., "Flow Cytometric analysis of Th1 and Th2 cytokines in PBMCs as a parameter of immunological dysfunction in patients of Superficial Transitional cell carcinoma of bladder", *Cancer Immunol. Immunother.*, 2006, 55(6):734-743.
Agarwala et al., "Randomized phase III study of paclitaxel plus carboplatin with or without sorafenib as second-line treatment in patients with advanced melanoma," *J. Clin. Oncol.*, 2007, 25(18S):8510 (Abstract).
Anonymous, A Phase II, multicenter, randomized, double-blind placebo-controlled trial evaluating the efficacy and safety of bevacizumab in combination with carboplatin and paclitaxel chemotherapy for the first-line treatment of patients with metastatic melanoma, U.S. National Institutes of Health, 2007, 3 pages.
Anonymous, "Phase II trial of carboplatin, weekly paclitaxel and biweekly bevacizumab in patients with unresectable stage IV melanoma," U.S. National Institutes of Health, 2007, 4 pages.
Asadullah et al., "Interleukin-10 therapy—review of a new approach," *Pharmacol Rev.*, 2003, 55(2):241-269.
Atkins et al., "High-dose recombinant interleukin-2 therapy in patients with metastatic melanoma: long-term survival update," *Cancer J Sci Am.*, 2000, 6 Suppl 1:S11-14.
Atkins, "Interleukin-2: clinical applications," *Semin Oncol.*, 2002, 29(3 Suppl 7):12-27.
Balch et al., "The new melanoma staging system," *Semin Cutan Med Surg.*, 2003, 22(1):42-54.
Baumgartner et al., "Melanoma induces immunosuppresion by up-regulating FOXP3(+) regulatory T cells," *J Surg Res.*, 2007, 141(1):72-77.
Belani et al., "Multicenter, randomized trial for stage IIIB or IV non-small-cell lung cancer using weekly paclitaxel and carboplatin followed by maintenance weekly paclitaxel or observation," *J. Clin. Oncol.*, 2003, 21:2933-2939.
Bolstad et al., "A comparison of normalization methods for high density oligonucleotide array data based on variance and bias," *Bioinformatics*, 2003, 19:185-193.
Cao et al., "Response of resistant melanoma to a combination of weekly paclitaxel and bevacizumab," Clin Transl Oncol, 2007, 9:119-120.
Carson et al., "A phase 2 trial of a recombinant humanized monoclonal anti-vascular endothelial growth factor (VEGF) antibody in patients with malignant melanoma," Proceedings of the ASCO vol. 22, No. 2873, General Poster Session, Thirty-Ninth Annual Meeting of the American Society of Clinical Oncology, May 31-Jun. 3, 2003, Chicago, IL, 2 pages.
Carson et al., "A phase 2 trial of a recombinant humanized monoclonal anti-vascular endothelial growth factor (VEGF) antibody in patients with malignant melanoma," Proc. Am. Soc. Clin. Oncol. 22: Abstract 2873 (2003).
Celis, "Overlapping human leukocyte antigen class I/II binding peptide vaccine for the treatment of patients with stage IV melanoma: evidence of systemic immune dysfunction, " *Cancer*, 2007, 110(1):203-214.
Chisholm et al., "Response to influenza immunisation during treatment for cancer," *Arch. Dis Child*, 2001, 84(6):496-500.
Chong and Morse "Combining cancer vaccines with chemotherapy," *Expert Opin Pharmacother.*, 2006, 6(16):2813-2820.
Demirkesen et al., "The correlation of angiogenesis with metastasis in primary cutaneous melanoma: a comparative analysis of microvessel density, expression of vascular endothelial growth factor and basic fibroblastic growth factor," *Pathology*, 2006, 38:132-137.
Denardo and Coussens, "Inflammation and breast cancer. Balancing immune response: crosstalk between adaptive and innate immune cells during breast cancer progression," *Breast Cancer Res.*, 2007, 9(4):212.
Desai et al., "Increased antitumor activity, intratumor paclitaxel concentrations, and endothelial cell transport of cremophor-free, albumin-bound paclitaxel, ABI-007, compared with cremophor-based paclitaxel," Clin Cancer Res., 2006, 12(4):1317-24.
Dudek et al., "Autologous large multivalent immunogen vaccine in patients with metastatic melanoma and renal cell carcinoma," *Am. J. Clin. Oncol.*, Apr. 1, 2008, 31(2):173-181.
ElBayoumi and Torchilin, "Tumor-Targeted Nanomedicines: Enhanced Antitumor Efficacy In vivo of Doxorubicin-Loaded, Long-Circulating Liposomes Modified with Cancer-Specific Monoclonal Antibody," *Clin Cancer Res.*, 2009, 15(6):1973-1980.
Ellyard et al., "Th2-mediated anti-tumour immunity: friend or foe?" *Tissue Antigens*, 2007, 70(1):1-11.
Elsadek and Kratz, "Impact of albumin on drug delivery—New applications on the horizon," *J of Controlled Release*, 2011, 1-25.
Ferrara et al., "The biology of VEGF and its receptors," *Nat. Med.*, 2003, 9:669-676.
Folkman, J. "Angiogenesis in cancer, vascular, rheumatoid and other disease," *Nat. Med.*, 1995, 1, 27-31.
Fricke et al., "Vascular endothelial growth factor-trap overcomes defects in dendritic cell differentiation but does not improve antigen-specific immune responses," *Clin. Cancer Res.*, 2007, 13:4840-4848.
Gabrilovich et al., "Production of vascular endothelial growth factor by human tumors inhibits the functional maturation of dendritic cells," *Nat. Med.*, 1996, 2:1096-1103.
Gao et al., "In vivo cancer targeting and imaging with semiconductor quantom dots," *Nat Biotech*, 2004, 22(8):969-976.
Gogas et al., "Chemotherapy for metastatic melanoma: time for a change?" Cancer, 2007, 109(3):455-464.
Graells et al., "Overexpression of VEGF$_{165}$ concomitantly expressed with its receptors promotes growth and survival of melanoma cells through MAPK and PI3K signaling," *J. Invest. Dermatol.*, 2004, 123:1151-1161.
Haley and Frenkel, "Nanoparticles for drug delivery in cancer treatment," *Urol. Oncol.: Seminars and Original Invest.*, 2008, 26:57-64.
Hauschild et al., "Individualized therapy of disseminated cancer using malignant melanoma as a model," Cancer and Metastasis Reviews, 2006, 25(2): 253-256.

(56) References Cited

OTHER PUBLICATIONS

Hersh et al., "Open-label, multicenter, phase II trial of ABI-007 in previously treated and previously untreated patients with metastatic malignant melanoma," *J. Clin. Oncol.*, 2005, 23(16S):7558 (Abstract).

Hodi et al., "Phase II study of paclitaxel and carboplatin for malignant melanoma," *Am. J. Clin. Oncol.*, 2002, 25:283-286.

Huncharek et al., "Single-agent DTIC versus combination chemotherapy with or without immunotherapy in metastatic melanoma: a meta-analysis of 3273 patients from 20 randomized trials," Melanoma Research, 11:75-81 (2001).

Inagaki et al., "Clinical signifigance of serum Th1-, Th2- and regulatory T cells-associated cytokines in adult T-cell leukemia/lymphoma: High interleukin-5 and -10 levels are significant unfavorable prognostic factors," *Int. J. Cancer*, 2006, 118(12):3054-3061.

Jiang and Chess, "Regulation of immune responses by T cells," N Engl J Med., 2006, 354(11):1166-1176.

Kamat et al., "Metronomic chemotherapy enhances the efficacy of antivascular therapy in ovarian cancer," *Cancer Res.*, 2007, 67(1):281-288.

Kawai et al., "VEGF121 promotes lymphangiogenesis in the sentinel lymph nodes of non-small cell lung carcinoma patients," *Lung Cancer*, 2008, 59(1):41-47.

Kikuchi et al., "Vascular endothelial growth factor and dendritic cells in human squamous cell carcinoma of the oral cavity," *Anticancer Res.*, 2006, 26(3A):1833-1848.

Kirkwood et al., "A pooled analysis of eastern cooperative oncology group and intergroup trials of adjuvant high-dose interferon for melanoma," Clin Cancer Res., 2004, 10(5):1670-1677.

Korman et al., "Tumor immunotherapy: preclincal and clincal activity of anti-CTLA4 antibodies," *Curt Opin Invest Drugs*, 2005, 6(6):582-591.

Krishnan et al., "Programmed death-1 receptor and interleukin-10 in liver transplant recipients at high risk for late cytomegalovirus disease," *Transpl Infect Dis.*, 12(4):363-70, print Aug. 2010, ePub Jan. 2010.

Kukowska-Latallo et al., "Nanoparticle Targeting of Anticancer Drug Improves Therapeutic Response in Animal Model of Human Epithelial Cancer," *Cancer Res*, 2005, 65(12):5317-5324.

Kumar et al., "Th1/Th2 cytokine imbalance in meningioma, anaplastic astrocytoma and glioblastoma multiforme patients," *Oncol. Rep.*, 2006, 15(6):1513-1516.

Lau et al., "Is inhibition of cancer angiogenesis and growth by paclitaxel schedule dependent?" *Anti-Cancer Drugs*, 2004, 15:871-875.

Lei et al., "Comparing cellular uptake and cytotoxicity of targeted drug carriers in cancer cell lines with different drug resistance mechanisms," *Nanomed: Nanotech, Biol, and Med.*, 2011, 7:324-332.

Lev et al., "Dacarbazine causes transcriptional up-regulation of interleukin 8 and vascular endothelial growth factor in melanoma cells: a possible escape mechanism from chemotherapy," *Mol. Cancer Ther.*, 2003, 2:753-763.

Lev et al., "Exposure of melanoma cells to decarbazine results in enhanced tumor growth and metastasis in vivo," *J. Clin. Oncol.*, 2004, 22:2092-2100.

Marcoval et al., "Angiogenesis and malignant melanoma. Angiogenesis is related to the development of vertical (tumorigenic) growth phase," *J. Cutan. Pathol.*, 1997, 24:212-218.

Markovic et al., "A phase II study of ABT-510 (thrombospondin-1 analog) for the treatment of metastatic melanoma," *Am. J. Clin. Oncol.*, 2007, 30(3):303-309.

Markovic et al., "A reproducible method for the enumeration of functional (cytokine producing) versus non-functional peptide-specific cytotoxic T lymphocytes in human peripheral blood," *Clin. Exp. Immunol.*, 2006, 145:438-447.

Markovic et al., "Peptide vaccination of patients with metastatic melanoma: improved clinical outcome in patients demonstrating effective immunization," *Am J Clin Oncol.*, 2006, 29(4):352-360.

Matsuda et al., "Preoperative oral immune-enhancing nutritional supplementation corrects TH1/TH2 imbalance in patients undergoing elective surgery for colorectal cancer," *Dis. Colon Rectum*, 2006, 49(4):507-516.

McElroy et al., "Imaging of Primary and Metastatic Pancreatic Cancer Using a Fluorophore-Conjugated Anti-CA19-9 Antibody for Surgical Navigation," *World J Surg.*, 2008, 32:1057-1066.

Melcher, "Recommendations for influenza and pneumococcal vaccinations in people receiving chemotherapy," *Clin Oncol (R Coll Radiol)*, 2005, 17(1): 12-15.

Merchan et al., "Increased endothelial uptake of paclitaxel as a potential mechanism for its antiangiogenic effects: potentiation by Cox-2 inhibition," *Int. J. Cancer*, 2005, 113:490-498.

Middleton et al., "Randomized phase III study of temozolomide versus dacarbazine in the treatment of patients with advanced metastatic malignant melanoma," *J. Clin. Oncol.*, 2000, 18:158-166.

Mimura et al., "Vascular endothelial growth factor inhibits the function of human mature dendritic cells mediated by VEGF receptor-2," *Cancer Immunol Immunother.*, 2007, 56(6):761-770.

Mocellin et al., "Cytokines and immune response in the tumor microenvironment," *J. Immunother.*, 2001, 24(5):392-407.

Motl, S., "Bevacizumab in combination chemotherapy for colorectal and other cancers," *Am. J. Health-Syst. Pharm*, 2005, 62:1021-1032.

Ng et al., "Influence of formulation vehicle on metronomic taxane chemotherapy: albumin-bound versus cremophor EL-based paclitaxel," *Clin. Cancer Res.*, 2006, 12:4331-4338.

Ng et al., "Taxane-mediated antiangiogenesis in vitro: influence of formulation vehicles and binding proteins," *Cancer Res.*, 2004, 64:821-824.

Oku et al., "Tumor growth modulation by sense and antisense vascular endothelial growth factor gene expression: effects on angiogenesis, vascular permeability, blood volume, blood flow, fluorodeoxyglucose uptake, and proliferation of human melanoma intracerebral xenografts," *Cancer Res.*, 1998, 58:4185-4192.

Parikh and Ellis, "The vascular endothelial growth factor family and its receptors," *Hematol. Oncol. Clin. N. Am.*, 2004, 18:951-971.

Park et al., "Anti-HER2 Immunoliposomes: Enhanced Efficacy Attributable to Targeted Delivery," *Clin. Cancer Res.*, 2002, 8:1172-1181.

Perez et al., "Phase 2 trial of carboplatin, weekly paclitaxel, and biweekly bevacizumab in patients with unresectable stage IV melanoma: a north central cancer treatment group study," Cancer, 2009, 115(1): 119-127.

Phase II: A Study of Bevacizumab With Carboplatin and Paclitaxel Chemotherapy for the First-Line Treatment of Patients With Metastatic Melanoma (BEAM) Mar. 12, 2007, [retrieved Mar. 15, 2010]. Retrieved from the Internet: <URL: http://clinicaltrials.gov/archive/NCT00434252/2007_03_12>, 3 pages.

Polak et al., "Mechanisms of local immunosuppression in cutaneous melanoma," *Br J Cancer*, 2007, 96(12):1879-1887.

Porrata and Markovic, "Timely reconstitution of immune competence affects clinical outcome following autologous stem cell transplantation," *Clin Exp Med.*, 2004, 4(2):78-85.

Porrata et al., "Early lymphocyte recovery predicts superior survival after autologous hematopoietic stem cell transplantation in multiple myeloma or non-Hodgkin lymphoma," *Blood*, 2001, 98(3):579-585.

Powell et al., "Adoptive transfer of vaccine-induced peripheral blood mononuclear cells to patients with metastatic melanoma following lymphodepletion," *J Immunol.*, 2006, 177(9):6527-6539.

Pries and Wollenberg, "Cytokines in head and neck cancer," *Cytokine Growth Factor Rev.*, 2006, 17(3):141-146.

Ranieri et al., "Vascular endothelial growth factor (VEGF) as a target of bevacizumab in cancer: from the biology to the clinic," *Curr. Med. Chem.*, 2006, 13:1845-1857.

Rao et al., "Combination of paclitaxel and carboplatin as second-line therapy for patients with metastatic melanoma," *Cancer*, 2006, 106:375-382.

Ribas et al., "Antitumor activity in melanoma and anti-self responses in a phase I trial with the anti-cytotoxic T lymphocyte-associated antigen 4 monoclonal antibody CP-675,206," *J Clin Oncol.*, 2005, 23(35):8968-8977.

(56) References Cited

OTHER PUBLICATIONS

Rosenberg et al., "Tumor progression can occur despite the induction of very high levels of self/tumor antigen-specific CD8+ T cells in patients with melanoma," *J. Immunol.*, 2005, 175(9):6169-6176.

Roy et al., "Tumor associated release of interleukin-10 alters the prolactin receptor and down-regulates prolactin responsiveness of immature cortical thymocytes," *J Neuroimmunol.*, 2007, 186(1-2):112-120.

Salven et al., "Enhanced expression of vascular endothelial growth factor in metastatic melanoma," *Br. J. Cancer*, 1997, 76:930-934.

Sandler et al., "Paclitaxel-carboplatin alone or with bevacizumab for non-small-cell lung cancer," *N. Engl. J. Med.*, 2006, 355:2542-2550.

Sato et al., "Intraepithelial CD8+ tumor-infiltrating lymphocytes and a high CD8+/regulatory T cell ratio are associated with favorable prognosis in ovarian cancer," *Proc Natl Aead Sci USA*, 2005, 102(51):18538-18543.

Sester et al., Differences in CMV-specific T-cell levels and long-term susceptibility to CMV infection after kidney, heart and lung transplantation, *Am J Transplant.*, 5(6):1483-1489, Jun. 2005.

Srivastava et al., "Angiogenesis in cutaneous melanoma: pathogenesis and clinical implications," *Microsc. Res. Tech.*, 2003, 60:208-224.

Streit and Detmar, "Angiogenesis, lymphangiogenesis, and melanoma metastasis," *Oncogene*, 2003, 22:3172-3179.

Taieb et al., "Chemoimmunotherapy of tumors: Cyclophosphamide synergtizes with exoxome based vaccines," *J. Immunol.*, Mar. 1, 2006, 176(5):2722-2729.

Tao et al., "Inhibiting the growth of malignant melanoma by blocking the expression of vascular endothelial growth factor using an RNA interference approach," *Br. J. Dermatol.*, 2005, 153:715-724.

Tas et al., "Circulating serum levels of angiogenic factors and vascular endothelial growth factor receptors 1 and 2 in melanoma patients," *Melanoma Res.*, 2006, 16:405-411.

Terheyden et al., "Anti-vascular endothelial growth factor antibody bevacizumab in conjunction with chemotherapy in metastasizing melanoma," Journal of Cancer Research and Clinical Oncology, 2007, 133(11): 897-901.

Ugurel et al., "Increased serum concentration of angiogenic factors in malignant melanoma patients correlates with tumor progression and survival," *J. Clin. Oncol.*, 2001, 19:577-583.

Vacca et al., "Docetaxel versus paclitaxel for antiangiogenesis," *J. Hematother. Stem Cell Res.*, 2002, 11:103-118.

Varker et al., "A randomized phase 2 trial of bevacizumab with or without daily low-dose interferon alfa-2b in metastatic malignant melanoma," *Ann Surg Oncol.*, 14(8):2367-2376, print Aug. 2007, Epub May 2007.

Vence et al., "Circulating tumor antigen-specific regulatory T cells in patients with metastatic melanoma," *Proc Natl Acad Sci USA*, 2007, 104(52): 20884-20889.

Walker and Disis, "Monitoring immune responses in cancer patients receiving tumor vaccines," *Int Rev Immunol.*, 2003, 22(3-4):283-319.

Wang et al., "Biofunctionalized targeted nanoparticles for therapeutic applications," *Expert Opin. Biol. Ther.*, 2008, 8(8):1063-1070.

Wang et al., "Paclitaxel at ultra low concentrations inhibits angiogenesis without affecting cellular microtubule assembly," *Anti-Cancer Drugs*, 2003, 14:13-19.

Weber, "Review: anti-CTLA-4 antibody ipilimumab: case studies of clinical response and immune-related adverse events," *Oncologist*, 12(7):864-872, Jul. 2007.

Wong et al., "Programmed death-1 blockade enhances expansion and functional capacity of human melanoma antigen-specific CTLs," *Int. Immunol.*, 2007, 19:1223-1234.

Yee et al., "Adoptive T cell therapy using antigen-specific CD8+ T cell clones for the treatment of patients with metastatic melanoma: in vivo persistence, migration, and antitumor effect of transferred T cells," *Proc Natl Acad Sci USA*, 2002, 99(25):16168-16173.

Zimpfer-Rechner et al., "Randomized phase II study of weekly paclitaxel versus paclitaxel and carboplatin as second-line therapy in disseminated melanoma: a multicentre trial of the Dermatologic Cooperative Oncology Group (DeCOG)," *Melanoma Res.*, 2003, 13:531-536.

"Concurrent Infusions," *J Oncol Pract.*, 4(4): 171, Jul. 2008.

Boasberg et al., "Nab-paclitaxel and bevacizumab as first-line therapy in patients with unresectable stage III and IV melanoma," *J Clin Oncol.*, 27:15s, 2009 (suppl; abstr 9061), 2009 ASCO Annual Meeting, Retrieved from the Internet: <URL: http://meetinglibrary.asco.org/print/584876>, 2 pages, 2009.

Davis, "Affinity separation of antibody-toxin conjugate from albumin-stabilized formulation," *Am Biotechnol Lab.*, 12(4):60-64, Mar. 1994.

de Weers et al., "Daratumumab, a novel therapeutic human CD38 monoclonal antibody, induces killing of multiple myeloma and other hematological tumors," *J. Immunol.*, 186(3): 1840-1848, Feb. 1, 2011.

Kondejewski et al., "Synthesis and characterization of carbohydrate-linked murine monoclonal antibody K20-human serum albumin conjugates," *Bioconjug Chem.*, 5(6):602-611, Nov.-Dec. 1994.

Kottschade et al., "A phase II trial of nab-paclitaxel (ABI-007) and carboplatin in patients with unresecatble stage IV melanoma : a North Central Cancer Treatment Group Study, N057E(1)," *Cancer*, 117(8):1704-10. Epub Nov. 8, 2010.

Kratz and Beyer, "Serum patients as drug carriers of anticancer agents: a review," *Drug Deliv.*, 5(4):281-299, 1998.

Kratz, "Albumin as a drug carrier: design of prodrugs, drug conjugates and nanoparticles," *J Control Release.*, 132(3):171-183, Epub May 17, 2008.

Wagner et al., "Enhanced drug targeting by attachment of an anti alphav integrin antibody to doxorubicin loaded human serum albumin nanoparticles," *Biomaterials.*, 31(8):2388-2398, Epub Dec. 23, 2009.

European Search Report for Application No. 12781802.9 dated Dec. 18, 2014, 7 pages.

Office Action in U.S. Appl. No. 14/309,617, mailed Oct. 1, 2014, 14 pages.

Office Action in U.S. Appl. No. 14/116,619 mailed Feb. 4, 2015, 8 pages.

International Preliminary Report on Patentability for PCT/US2013/062638, issued Apr. 16, 2015, 12 pages.

International Search Report and Written Opinion for PCT/US2013/062638, mailed Jan. 23, 2014, 8 pages.

Connick et al., "Immune reconstitution inflammatory syndrome associated with Kaposi sarcoma during potent antiretroviral therapy," Clin Infect Dis., 39(12)1852-1855, Epub Nov. 19, 2004.

Gonzalez-Cao et al., "Preliminary results of the combination of bevacizumab and weekly Paclitaxel in advanced melanoma," Oncology, 74(1-2):12-16, Epub Jun. 9, 2008.

O'Day et al., "S2. Subgroup analysis of efficacy and safety analysis of a randomized, double-blinded controlled phase 2 study of STA-4783 in combination with paclitaxel in patients with metastatic melanoma," Arch Dermatol Research, 299(5-6):294, 2007.

Rudy et al., "Cephalostatin-2 potentiates apoptosis induced by paclitaxel in the melanoma cell line sk-mel5*" "Naunyn-Schmiedeberg's Archives of Pharmacology," 372(S1):103, Abstract 389, 2006.

Somlo et al., "High-dose paclitaxel in combination with doxorubicin, cyclophosphamide and peripheral blood progenitor cell rescue in patients with high-risk primary and responding metastatic breast carcinoma: toxicity profile, relationship to paclitaxel pharmacokinetics and short-term outcome," Br J Cancer., 84(12):1591-1596, Jun. 15, 2001.

Zagozdzon et al., "Potentiation of antitumor effects of IL-12 in combination with paclitaxel in murine melanoma model in vivo," Int J Mol Med., 4(6)-645-648, Dec. 1999.

Zhang et al., "Experimental study of apoptosis induced by paclitaxel in human melanoma A375 cell," J. China Medical University, 35(2):134-136, 2006 [English abstract].

Office Action in European Application No. 09774506.1 dated Jan. 8, 2016, 7 pages.

METHODS FOR REDUCING GLOBAL CHRONIC INFLAMMATION AND THE PRESENCE OF MELANOMA

CROSS-REFERENCE TO RELATED APPLICATIONS

This application is a continuation of U.S. application Ser. No. 12/979,105, filed Dec. 27, 2010, which is a continuation-in-part of International Application No. PCT/US2009/049511, filed Jul. 2, 2009, which claims the benefit of priority from U.S. Provisional Application Ser. No. 61/078,203, filed on Jul. 3, 2008. The disclosures of the prior applications are considered part of (and are incorporated by reference in) the disclosure of this application.

BACKGROUND

1. Technical Field

This document relates to methods and materials involved in treating cancer (e.g., melanoma). For example, this document relates to methods and materials involved in using an anti-chronic inflammation treatment (e.g., chemotherapy) in combination with a cancer treatment agent (e.g., a cancer vaccine) to treat cancer.

2. Background Information

Cancer is a serious illness that affects many people every year. Melanoma is the most serious form of skin cancer. It is a malignant tumor that originates in melanocytes, the cells which produce the pigment melanin that colors skin, hair, and eyes and is heavily concentrated in most moles. While it is not the most common type of skin cancer, melanoma underlies the majority of skin cancer-related deaths. About 48,000 deaths worldwide are registered annually as being due to malignant melanoma. Worldwide, there are about 160,000 new cases of melanoma each year. Melanoma is more frequent in white men and is particularly common in white populations living in sunny climates. Other risk factors for developing melanoma include a history of sunburn, excessive sun exposure, living in a sunny climate or at high altitude, having many moles or large moles, and a family or personal history of skin cancer.

SUMMARY

This document provides methods and materials related to treating cancer. For example, this document provides methods and materials for using an anti-chronic inflammation treatment (e.g., chemotherapy) in combination with a cancer treatment agent (e.g., a cancer vaccine) to treat cancer. As described herein, cancer can induce a global state of immune dysfunction and/or chronic inflammation in the cancer patient. This global state of immune dysfunction and/or chronic inflammation can prevent the patient from mounting a successful response against the cancer. For example, a cancer patient with a global state of chronic inflammation can be in a state such that the patient is unable to generate an anti-cancer immune response when given an anti-cancer vaccine. The methods and materials provided herein can be used to reduce the global state of immune dysfunction and/or chronic inflammation present within a cancer patient such that the cancer patient can better respond to a cancer treatment such as a cancer vaccine. As described herein, chemotherapy, radiation, anti-IL-4 agents (e.g., anti-IL-4 antibodies), anti-IL-13 agents (e.g., soluble IL-13 receptor), steroids, and combinations thereof can be used to reduce the global state of immune dysfunction and/or chronic inflammation present within a cancer patient. Once the global state of immune dysfunction and/or chronic inflammation present within a cancer patient is reduced, the cancer patient can be treated with an appropriate cancer treatment such as a cancer vaccine or other immune stimulating agents (e.g., IL-2 or IL-12).

In general, this document features a method for treating a mammal having cancer. The method comprises, or consists essentially of, (a) administering to the mammal an anti-chronic inflammation treatment under conditions wherein the level of global chronic inflammation in the mammal is reduced, and (b) administering to the mammal a cancer treatment agent under conditions wherein the presence of the cancer is reduced. The mammal can be a human. The cancer can be melanoma. The cancer can be stage IV melanoma. The anti-chronic inflammation treatment can comprise chemotherapy, radiation, an anti-IL-4 agent, an anti-IL-13 agent, or a steroid treatment. The cancer treatment agent can be a cancer vaccine. The cancer vaccine can be a MART-1, gp100, or survivin cancer vaccine. The period of time between the last administration of the anti-chronic inflammation treatment and the first administration of the cancer treatment agent can be between two weeks and six months.

In another aspect, this document features a method for treating a mammal having cancer. The method comprises, or consists essentially of, (a) administering to the mammal an anti-TGFβ antibody under conditions wherein the level of global chronic inflammation in the mammal is reduced, and (b) administering to the mammal a cancer treatment agent under conditions wherein the presence of the cancer is reduced. The mammal can be a human. The cancer can be melanoma. The cancer can be stage IV melanoma. The cancer treatment agent can be a cancer vaccine. The cancer vaccine can be a MART-1, gp100, or survivin cancer vaccine. The period of time between the last administration of the anti-TGFβ antibody and the first administration of the cancer treatment agent can be between two weeks and six months.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
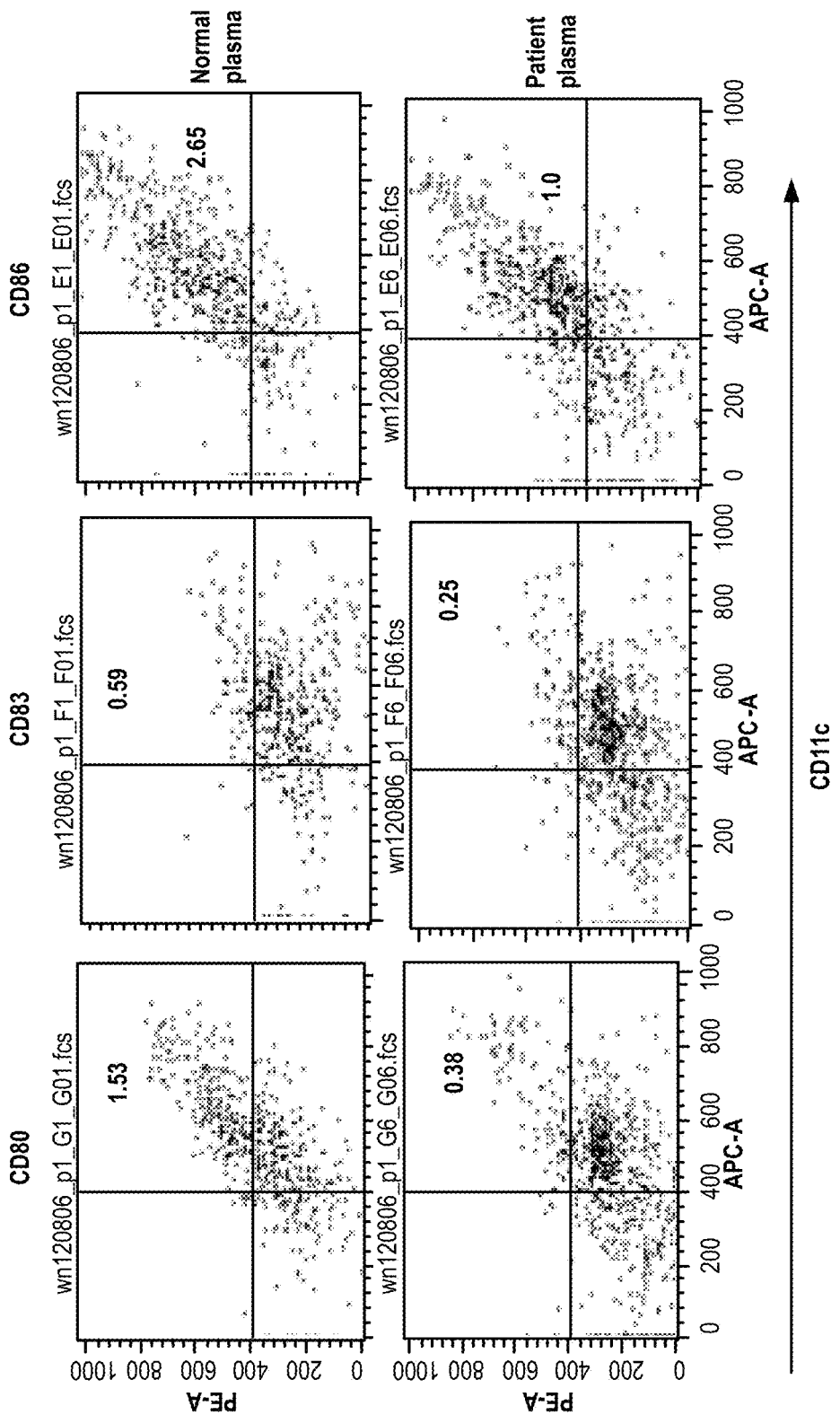
FIG. 1: Effects of 1% patient plasma (vs. normal plasma) on in vitro maturation of normal DC. Presented is a representative experiment demonstrating the % co-stimulatory molecule positive (CD80, 83, 86) DC.

This document provides methods and materials related to treating cancer in mammals. For example, this document provides methods and materials related to the use of an anti-chronic inflammation treatment (e.g., chemotherapy) in combination with a cancer treatment agent (e.g., a cancer vaccine) to treat cancer.

The methods and materials provided herein can be used to treat cancer in any type of mammal including, without limitation, mice, rats, dogs, cats, horses, cows, pigs, monkeys, and humans. Any type of cancer, such as skin cancer (e.g., melanoma), can be treated. Examples of cancer that can be treated as described herein include, without limitation, skin cancer, lung cancer, breast cancer, prostate cancer, ovarian cancer, and colon cancer. In some cases, stage I, stage II, stage III, or stage IV melanoma can be treated using the methods and materials provided herein.

In general, cancer can be treated by administering an anti-chronic inflammation treatment such that the global state of immune dysfunction and/or chronic inflammation present within a cancer patient is reduced. For example, chemotherapy, radiation, anti-IL-4 agents (e.g., anti-IL-4 antibodies), anti-IL-13 agents (e.g., soluble IL-13 receptor), steroids, and combinations thereof can be used to reduce the global state of immune dysfunction and/or chronic inflammation present within a cancer patient. In some cases, chemotherapy such as paclitaxel, carboplatin, temozolomide, or cyclophosphamide can be administered to a cancer patient to reduce the global state of immune dysfunction and/or chronic inflammation present within a cancer patient. In some cases, an anti-chronic inflammation treatment can include, without limitation, administering an anti-TGFβ antibody. For example, anti-TGFβ antibodies can be administered to a cancer patient to reduce the global state of immune dysfunction and/or chronic inflammation present within a cancer patient. Examples of anti-TGFβ antibodies include, without limitation, human monoclonal anti-TGF-β1 antibodies such as CAT-192 (Genzyme Inc.).

Any appropriate method can be used to assess whether or not the global state of immune dysfunction and/or chronic inflammation was reduced following an anti-chronic inflammation treatment. For example, cytokine profiles (e.g., IL-4, IL-13, IL-4, IL-13, IL-5, IL-10, IL-2, and interferon gamma) present in blood can be assessed before and after an anti-chronic inflammation treatment to determine whether or not the global state of immune dysfunction and/or chronic inflammation was reduced.

Once the global state of immune dysfunction and/or chronic inflammation present within a cancer patient is reduced, the cancer patient can be treated with an appropriate cancer treatment (e.g., an immune cancer treatment) such as a cancer vaccine. Examples of appropriate cancer treatment agents include, without limitation, immune stimulating cytokines (e.g., IL-2, IL-12, interferon alpha, and interferon gamma), inhibitors of immune down-regulation (e.g., anti-CTLA4, anti-41bb, anti-PD-1, and anti-CD25), and cancer vaccines (e.g., MART-1, gp100, survivin, and tyrosinase cancer vaccines). It will be appreciated that paclitaxel, carboplatin, bevacizumab, and anti-CTLA-4 can be used to treat (e.g., skin cancer) upon administration either individually or in any combination thereof (e.g., paclitaxel, carboplatin and bevacizumab).

In some cases, the amount of time between administration of an anti-chronic inflammation treatment and administration of a cancer treatment can be between two weeks and twelve months (e.g., between two weeks and eleven months, between two weeks and ten months, between two weeks and nine months, between two weeks and eight months, between two weeks and seven months, between two weeks and six months, between one month and twelve months, between one month and six months, or between two months and six months). For example, a chemotherapy agent (e.g., paclitaxel) can be administered to a cancer patient to reduce the global state of immune dysfunction and/or chronic inflammation present within the cancer patient. Then, after one month without any type of anti-chronic inflammation treatment, a cancer treatment (e.g., a cancer vaccine) can be administered to the cancer patient.

Any appropriate method can be used to administer a cancer treatment agent to a mammal. For example, a cancer treatment agent can be administered orally or via injection (e.g., subcutaneous injection, intramuscular injection, intravenous injection, or intrathecal injection). In some cases, cancer treatment agents can be administered by different routes. For example, one cancer treatment agent can be administered orally and a second cancer treatment agent can be administered via injection.

In some cases, a cancer treatment agent can be administered following resection of a tumor. Cancer treatment agent can be administered to a mammal in any amount, at any frequency, and for any duration effective to achieve a desired outcome (e.g., to increase progression-free survival or to increase the time to progression). In some cases, cancer treatment agents can be administered to a mammal having skin cancer to reduce the progression rate of melanoma by 5, 10, 25, 50, 75, 100, or more percent. For example, the progression rate can be reduced such that no additional cancer progression is detected. Any method can be used to determine whether or not the progression rate of skin cancer is reduced. For example, the progression rate of skin cancer can be assessed by imaging tissue at different time points and determining the amount of cancer cells present. The amounts of cancer cells determined within tissue at different times can be compared to determine the progression rate. After treatment as described herein, the progression rate can be determined again over another time interval. In some cases, the stage of skin cancer after treatment can be determined and compared to the stage before treatment to determine whether or not the progression rate was reduced.

In some cases, a cancer treatment agent can be administered to a mammal having cancer under conditions where progression-free survival or time to progression is increased (e.g., by 5, 10, 25, 50, 75, 100, or more percent) as compared to the median progression-free survival or time to progression, respectively, of corresponding mammals having untreated cancer.

An effective amount of a cancer treatment agent can be any amount that reduces the progression rate of cancer, increases the progression-free survival rate, or increases the median time to progression without producing significant toxicity to the mammal. Typically, an effective amount of a cancer treatment agent such as bevacizumab can be from about 5 mg/kg/week to about 15 mg/kg/week (e.g., about 10 mg/kg/week). If a particular mammal fails to respond to a particular amount, then the amount of one or more of the compounds can be increased by, for example, two fold. After receiving this higher concentration, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the cancer may require an increase or decrease in the actual effective amount administered.

The frequency of administration can be any frequency that reduces the progression rate of cancer, increases the progression-free survival rate, or increases the median time to progression without producing significant toxicity to the mammal. For example, the frequency of administration can be from about once a month to about three times a month, or from about twice a month to about six times a month, or from about once every two months to about three times every two months. The frequency of administration can remain constant or can be variable during the duration of treatment. In addition, the frequency of administration of multiple cancer treatment agents can be the same or can differ. For example, one cancer treatment agent can be administered three times during a 28 day period, while a second cancer treatment agent can be administered one time, and third cancer treatment agent can be administered two times during the same period. A course of treatment with a cancer treatment agent can include rest periods. For example, a cancer treatment agent can be administered over a two week period followed by a two week rest period, and such a regimen can be repeated multiple times. As with the effective amount, various factors can influence the actual frequency of administration used for a particular application. For example, the effective amount, duration of treatment, use of multiple treatment agents, route of administration, and severity of the cancer may require an increase or decrease in administration frequency.

An effective duration for administering a composition provided herein can be any duration that reduces the progression rate of cancer, increases the progression-free survival rate, or increases the median time to progression without producing significant toxicity to the mammal. Thus, the effective duration can vary from several days to several weeks, months, or years. In general, the effective duration for the treatment of cancer can range in duration from several weeks to several months. In some cases, an effective duration can be for as long as an individual mammal is alive. Multiple factors can influence the actual effective duration used for a particular treatment. For example, an effective duration can vary with the frequency of administration, effective amount, use of multiple treatment agents, route of administration, and severity of the cancer.

After administering a composition provided herein to a mammal, the mammal can be monitored to determine whether or not the cancer was treated. For example, a mammal can be assessed after treatment to determine whether or not the progression rate of cancer was reduced (e.g., stopped). As described herein, any appropriate method can be used to assess progression and survival rates.

The invention will be further described in the following examples, which do not limit the scope of the invention described in the claims.

EXAMPLES

Example 1

Patients, Methods, and Materials

Patients

Blood samples collected from patients with early stage melanoma (melanoma in situ and melanoma stage I, II and III) and benign nevi (atypical/dysplastic nevi) were newly diagnosed patients with no previous treatment. All patients were tumor free at the time of peripheral blood collection. Samples from patients with metastatic melanoma (newly diagnosed, previously untreated) as well as healthy volunteers/controls were collected under a separate melanoma blood and tissue banking protocol. Both protocols were reviewed and approved for use in these studies. All biospecimens were collected, processed, and stored in uniform fashion following established standard operating procedures. All patients signed an informed consent document. The presented study describes data obtained from 113 men and 96 women ranging in age from 21 to 85 (Table 1).

Collection of Plasma and Peripheral Blood Mononuclear Cells

Peripheral venous blood (50-90 mL) was drawn into heparinized Vacutainer tubes that were processed and separated into plasma and peripheral blood mononuclear cells (PBMC) following gradient centrifugation using Ficoll-Paque (GE Healthcare Uppsala, Sweden). Plasma was collected and immediately frozen at $-80°$ C. (1 mL aliquots). PBMC were collected, washed in phosphate buffered saline (PBS), counted, diluted to $1\times10^7$/mL and viably frozen in 90% cosmic calf serum (Hyclone Inc. Logan, Utah) and 10% DMSO (Sigma St. Louis, Mo.). All assays were batch-analyzed at the end of the study.

Immunophenotyping

The following anti-human monoclonal antibodies were used in PBMC immunophenotyping for flow cytometry: anti-CD3-APC, FITC and PE, anti-CD4-FITC, anti-CD8-PE, anti-CD16 PE, anti-CD56 PE, anti-CD62L APC, anti-CD69 FITC, anti-CD14 FITC, anti-CD16 FITC, anti-CD19 FITC, anti-CD11c APC, anti-CD80 PE, anti-CD83 PE, anti-CD86 PE, anti-CD40 APC, anti-HLA-DR PC5, anti-PD-1 (BD Pharmingen San Jose, Calif.). The human monoclonal antibodies anti-CD4 PC5 and anti-CD25 PE were purchased from Biolegend (San Diego, Calif.) and used in conjunction with anti-human FoxP3 for the enumeration of $T_{reg}$ cells. The following anti-human monoclonal antibodies were used for intracellular staining for flow cytometry: anti-IFNγ FITC, anti-IL-13 PE, anti-IL-4 PE (R and D Systems Minneapolis, Minn.), and anti-FoxP3 Alexaflour 488 (Biolegend San Diego, Calif.).

Previously frozen PBMC ($0.5$-$1.0\times10^6$ cells/mL) were thawed and aliquoted into 96 well rounded bottom plates (100 μL/well). The desired antibody or antibody pool was added at 5 μL/well. The cells and antibodies were incubated for 30 minutes at 4° C. and washed twice with 1×PBS (Cellgro Manassas, Va.), 0.1% BSA and 0.05% sodium azide (Sigma St. Louis, Mo.). Four-color flow cytometry was performed on a LSRII flow cytometer (Becton Dickenson San Jose, Calif.), and Cellquest™ software (Becton Dickenson San Jose, Calif.; software for analyzing flow cytometry data) was utilized for data analysis. For dendritic cells, a gate was set on cells, which were HLA-DR$^+$ and Lin$^-$ (CD3, CD14, CD16 and CD19). From this population the percentage of cells,

TABLE 1

Study patient population distributed by clinical category, age, sex and assayed immune parameters.

| | | | | Assayed immune parameters | | | | |
|---|---|---|---|---|---|---|---|---|
| Clinical category | Total Patients | Age mean ± SD (range) | % female | Cell Subset | Plasma Cytokines | Tetramer | T-cell Function Assay | RNA array |
| Benign Nevi | 34 | 51 ± 12 (21-71) | 68 | 26 | 34 | 7 | 2 | 0 |
| Atypical/ Dysplastic | 25 | 52 ± 16 (25-84) | 44 | 22 | 16 | 11 | 1 | 0 |
| In situ melanoma | 36 | 61 ± 16 (26-84) | 36 | 30 | 35 | 16 | 3 | 0 |
| Stage I | 45 | 54 ± 17 (21-82) | 44 | 36 | 44 | 16 | 4 | 0 |
| Stage II | 16 | 55 ± 17 (22-81) | 44 | 11 | 12 | 9 | 0 | 0 |
| Stage III | 16 | 53 ± 19 (23-83) | 44 | 14 | 16 | 6 | 1 | 0 |
| Stage IV | 37 | 56 ± 14 (28-85) | 43 | 32 | 30 | 27 | 16 | 24 | which were CD11c⁺ and positive for costimulatory molecules (CD80, CD83 and CD86) was determined as previously elsewhere (Fricke et al., *Clin. Cancer Res.*, 13:4840-8 (2007)). A panel of tumor associated antigen tetramers, MART-1$_{26-35}$, gp100$_{264-272}$, gp100$_{209-217}$, and tyrosinase$_{369-377}$ (Beckman Coulter San Jose, Calif.) were used to enumerate the frequency of tumor antigen specific CD8 positive T-cells. Recall antigens, EBV$_{280-288}$ and CMV$_{495-503}$ (Beckman Coulter San Jose, Calif.) were used as positive controls. For tetramer frequencies, a gate was set on lymphocytes, which were CD8⁺ and negative for CD4, CD14 and CD19. Three-color flow cytometry was performed on a LSRII flow cytometer (Becton Dickenson San Jose, Calif.) and Cellquest™ software (Becton Dickenson San Jose, Calif.) was utilized for data analysis.

Functional enumeration of tumor antigen specific CTL was performed using an artificial antigen presenting cell method (aAPC) as described elsewhere (Markovic et al., *Clin. Exp. Immunol.*, 145:438-47 (2006)). Briefly, frozen PBMC were thawed, labeled with the desired tumor antigen peptide/class I tetramers (Beckman Coulter Fullerton, Calif.) and stimulated for 6 hours with streptavidin coated microbeads (Invitrogen Oslo, Norway) loaded with HLA-A2 class I containing tumor antigen peptides of choice (MART-1, gp100 or tyrosinase) and anti-human CD28 in the presence of brefeldin A (Sigma, St. Louis, Mo.). After stimulation, the cells were fixed with 2% paraformaldehyde (Sigma, St. Louis, Mo.) and then permeabilized with 0.1% saponin (Sigma, St. Louis, Mo.) in PBS. Cells were then immunophenotyped with anti-human CD4-PC5 or CD8-APC and intracellular staining was done with anti-human IFNγ FITC or IL-4 PE. Four-color flow cytometry was performed with a FACSCaliber™ (a flow cytometer) and Cellquest™ software (Becton Dickenson San Jose, Calif.) was utilized for data analysis.

Plasma Cytokine, Chemokines and Growth Factor Concentrations

Protein levels for 27 cytokines, chemokines, and growth factors, including IL-1β, IL-1ra, IL-2, IL-4, IL-5, IL-6, IL-7, IL-8, IL-9, IL-10, IL-12p70, IL-13, IL-15, IL-17, Eotaxin, FGF basic, G-CSF, GM-CSF, IFN-γ, IP-10, MCP-1, MIP-1α, MIP-1β, PDGF, RANTES, TNF-α, and VEGF, were measured using the Bio-plex cytokine assay (Bio-rad, Hercules, Calif.) as per manufacturer's instructions. Patient plasma was diluted 1:4 in dilution buffer and 50 μL was added to washed, fluorescently dyed microspheres (beads) to which biomolecules of interest are bound. The beads and diluted patient plasma were incubated for 30 minutes at room temperature with agitation. After the incubation the beads were washed in Bio-plex wash buffer and placed in 25 μL of detection antibody and incubated for 30 minutes as described above. After washing, the beads were placed in streptavidin-PE, incubated, and washed a final time. The bound beads were resuspended in 125 μL Bio-plex assay buffer and read with the Luminex plate reader (Bio-rad, Hercules, Calif.). Protein concentrations were determined using a standard curve generated using the high PMT concentrations with sensitivity from 10-1000 pg/mL.

VEGF Mediated T$_{h1}$/T$_{h2}$ Polarity

To determine the effect of VEGF on T$_{h1}$ and T$_{h2}$ polarity, PBMC from healthy donors were stimulated for 3 days with CD3/CD28 expander beads (Invitrogen Oslo, Norway) with and without increasing doses of recombinant VEGF (1-16 pg/mL). Cells were also cultured with 10 μg/mL recombinant human IL-12 (R and D Systems, Minneapolis, Minn.) or 8 μg/mL of a monoclonal anti-human IL-12 (R and D Systems Minneapolis, Minn. clone #24910). After the culture, the cells were harvested and restimulated with 50 ng/mL PMA (Sigma, St. Louis, Mo.) and 1 μg/mL ionomycin (Sigma, St. Louis, Mo.) in the presence of 10 μg/mL brefeldin A for 4 hours. The cells were then stained with anti-human CD4, anti-human IFN-γ and anti-human IL-4 flow cytometry.

Tumor Tissue RNA Extraction and Microarray

Frozen tissue sections of melanoma biopsies, were examined, regions of pure tumor with little/no evidence of necrosis or stromal infiltration were outlined, scraped off the slides, and used for RNA extraction. Total RNA was isolated from the excised tumor tissue using the Qiagen RNA extraction kit (Qiagen Valencia, Calif.). The quality of the RNA was evaluated by obtaining electropherograms on Agilent 2100 Bioanalyzer and RNA integrity number (RIN) using 2100 Expert software (Agilent Technologies, Inc. Palo Alto, Calif.). cDNA was prepared from a total of 10 μg of RNA. Samples were quantified using standard spectrophotometry using a Tecan spectrophotometer (Tecan US, Research Triangle Park, N.C.) and considered acceptable if the A260/280 reading was >1.7. The purified cDNA was used as a template for in vitro transcription reaction for the synthesis of biotinylated cRNA using RNA transcript labeling reagent (Affymetrix, Santa Clara, Calif.). Labeled cRNA was then fragmented and hybridized onto the U133 Plus 2.0 array. Appropriate amounts of fragmented cRNA and control oligonucleotide B2 were added along with control cRNA (BioB, BioC, and BioD), herring sperm DNA, and bovine serum albumin to the hybridization buffer. The hybridization mixture was heated at 99° C. for 5 minutes followed by incubation at 45° C. for 5 minutes before injecting the sample into the microarray. Then, the hybridization was carried out at 45° C. for 16 hours with mixing on a rotisserie at 60 rpm. After hybridization, the solutions were removed, and the arrays were washed and then stained with streptavidin-phycoerythrin (Molecular Probes, Eugene, Oreg.). After washes, arrays were scanned using the GeneChip Scanner 3000 (Affymetrix, Santa Clara, Calif.). The quality of the fragmented biotin labeled cRNA in each experiment was evaluated before hybridizing onto the U133A expression array by both obtaining electropherograms on Agilent 2100 Bioanalyzer and hybridizing a fraction of the sample onto test-3 array as a measure of quality control. GeneSpring GX 7.3 (Agilent Technologies, Inc. Santa Clara, Calif.) data analysis software was used to analyze the results of the microarray experiment. Gene expression values were normalized by the GCRMA algorithm (Bolstad et al., *Bioinformatics*, 19:185-93 (2003)).

Statistical Analysis

The majority of samples analyzed in this report were randomly assigned to batches for each laboratory assay due to the fact that all samples were not collected/processed at the same time. The randomization was stratified to assure an even distribution across the stages of disease for each batch. The distributions of the results of each run were examined, and those that did not appear to be normally distributed were transformed using either logarithmic or square root transformations. In order to look at differences in various parameters between stages of disease, analysis was performed utilizing analysis of covariance (ANCOVA), adjusting for age, gender, and batch effects. Results of this analysis were summarized by least square means and 95% confidence intervals for each stage of disease. The p-values presented are those from the overall ANCOVA, which compares the means levels of each parameter across all stages of disease. P-values<0.05 were considered to be statistically significant. Due to the magnitude of the cytokine data from the multiplex assay the data was processed using Partek 6.3 software (Partek Inc. St. Louis Mo.) and analyzed using a principal component analysis (PCA) approach. PCA was utilized in an effort to vector space transform a multidimensional data set representing 27 variables for each individual patient and group patients based on similar cytokine concentrations revealing the internal relationships of cytokines within patient groups (e.g., per stage of melanoma) in an unbiased way.

Example 2

Systemic Immune Dysfunction

Figure 2:
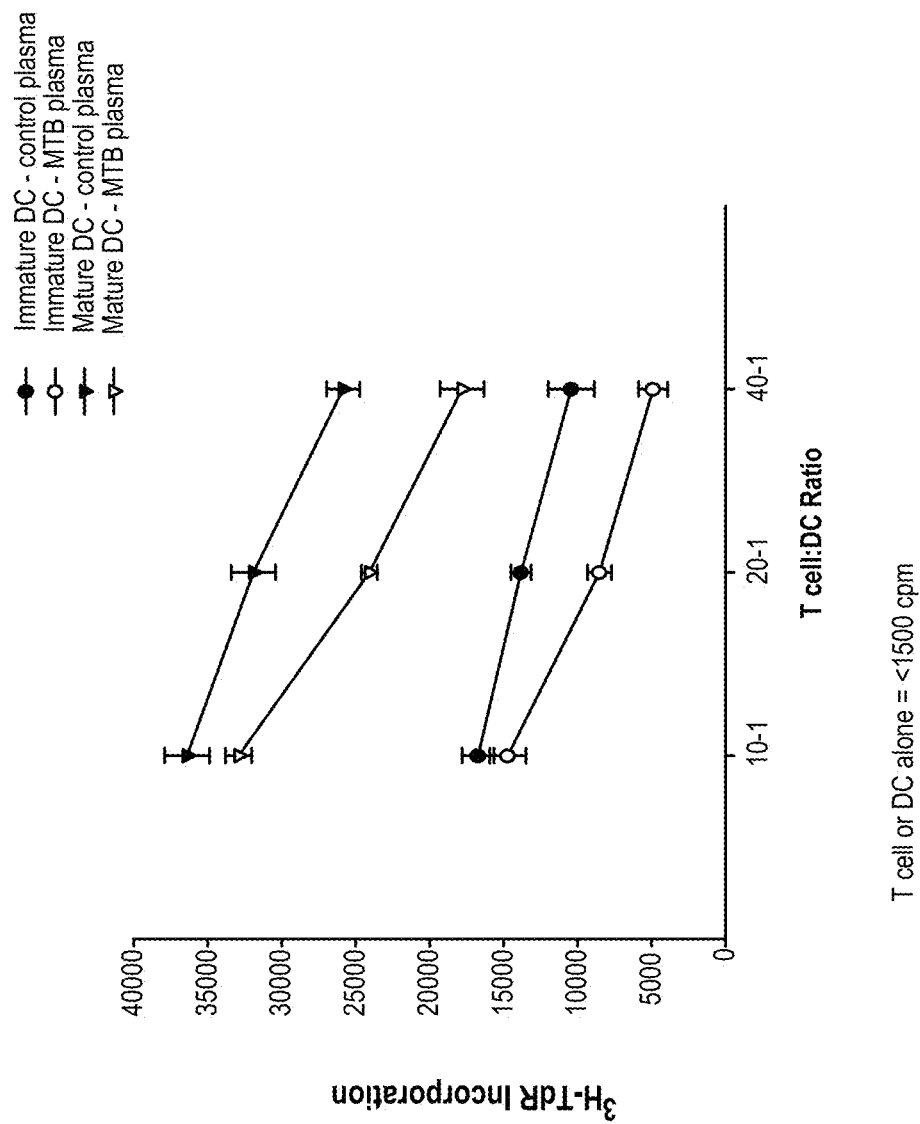
FIG. 2. Allogeneic mixed lymphocyte reaction cultures evaluating proliferation of T cells mixed at differing ratios with mature or immature dendritic cells in the presence of normal (control) plasma or plasma from a patient with metastatic melanoma (MTB plasma). T cell proliferation was assessed by 3H-TdR incorporation. Similar results were observed in two other experiments.

Preliminary results support the notion that systemic immune dysfunction can lead to the observed induction of tolerance following peptide vaccination in clinical trials. In this example, normal donor myeloid DC were exposed to in vitro culture conditions (GM-CSF, IL-4, and CD40L) that lead to their differentiation and maturation (expression of co-stimulatory molecules) (FIG. 1). The addition of patient plasma to these experimental conditions resulted in a significant reduction in the number of DC expressing key co-stimulatory molecules (maturation), suggesting the presence of a soluble inhibitor(s) of DC maturation. Similar observations, with varying degrees of "suppression" were made in another nine experiments (nine other samples of patient plasma). Even when normal DCs (mature or immature) were combined with other normal donor lymphocytes in a mixed lymphocyte culture, the presence of patient vs. normal plasma lead to significantly diminished lymphocyte proliferation (FIG. 2). Thus, factors in the plasma of patients with metastatic melanoma are interrupting normal immune cell function.

Example 3

Figure 3:
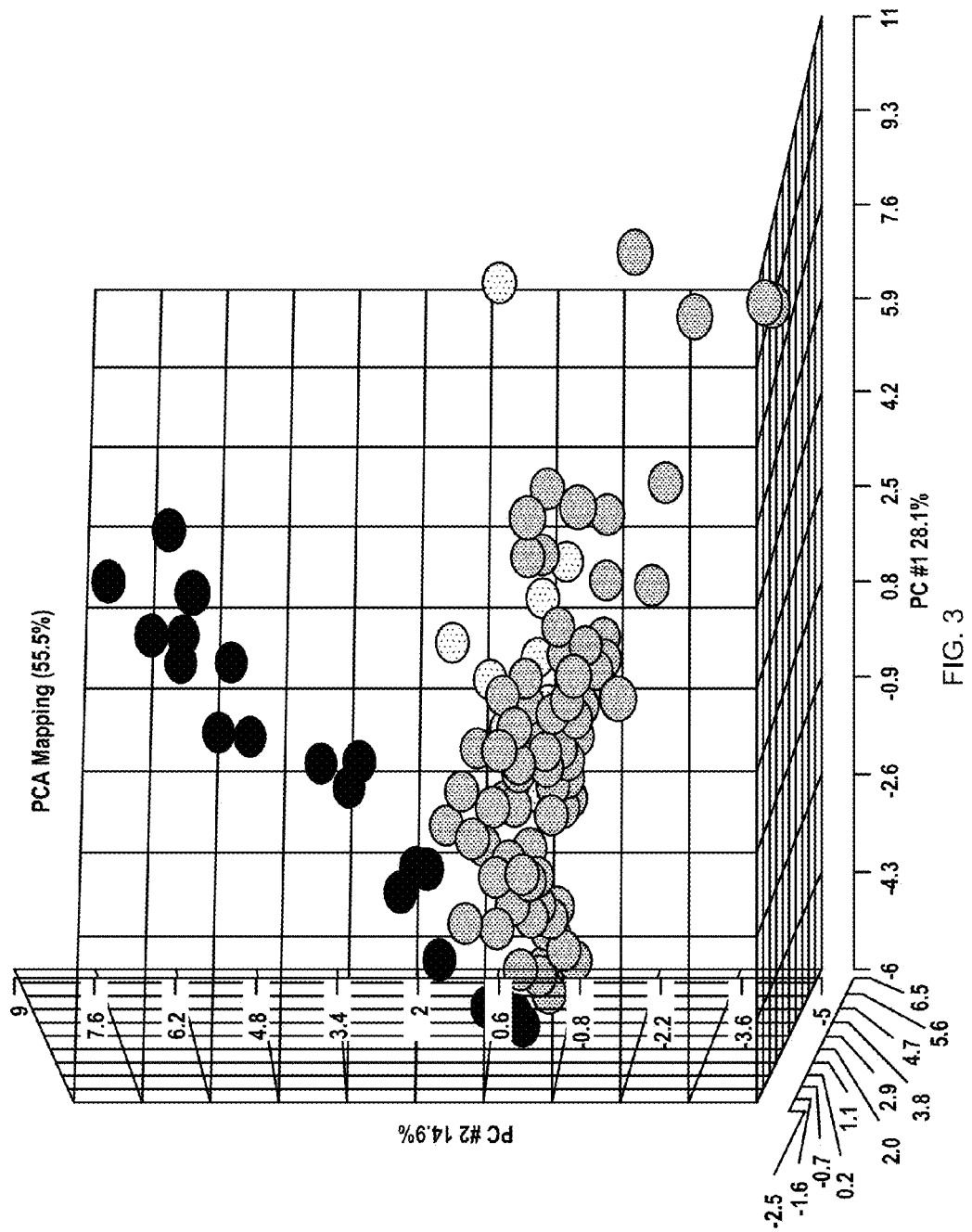
FIG. 3. Three dimensional representation of the results of Principal Component Analysis (PCA). The PCA was performed on 234 clinical samples for concentrations of 27 cytokines. Each sphere represents one clinical sample. The dark spheres represent stage IV melanoma patients, and the lighter spheres represent atypical nevi, benign nevi, in situ melanoma, stage I melanoma, stage II melanoma, or stage III melanoma. The axes are the main principal components. Significant grouping is only evident for patients in the cohort of stage IV (metastatic) melanoma (dark spheres).
Figure 4:
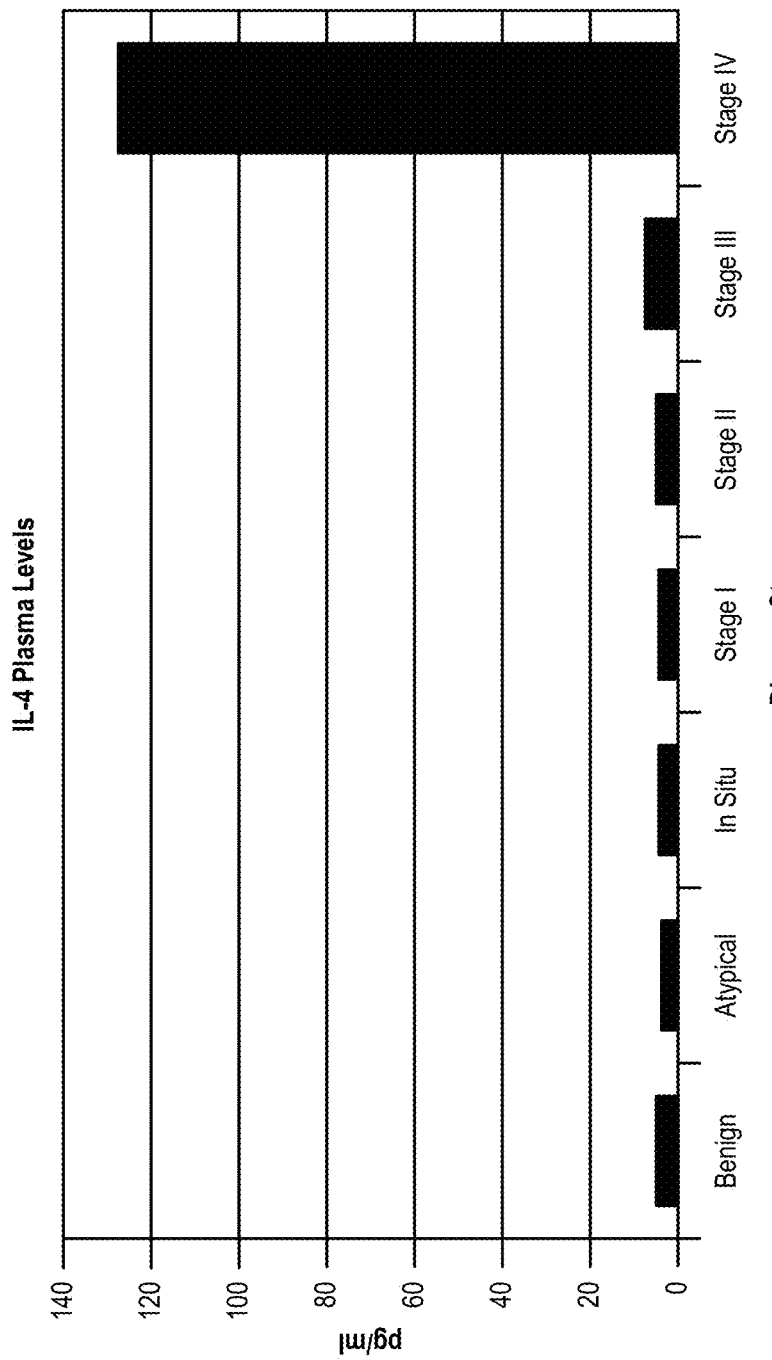
FIG. 4: Mean plasma IL-4 levels (pg/mL)±SD across stages of melanoma (melanoma in situ and stages: I, II, III, IV), patients with atypical nevi (atypical) and benign nevi (normal controls).

Evidence for Th2 Driven Systemic Chronic Inflammation in Patients with Metastatic (Stage IV) Melanoma The identity of the unknown factor(s) could be a known cytokine. Thus, a screening study was performed to quantify the plasma concentrations of 27 different cytokines (BioRad human 27-plex cytokine panel assaying for plasma concentrations of IL-1β, IL-1rα, IL-2, IL-4, IL-5, IL-6, IL-7, IL-8, IL-9, IL-10, IL-12(p70), IL-13, IL-15, IL-17, basic FGF, eotaxin, G-CSF, GM-CSF, IFN-γ, IP-10, MCP-1, MIP-1α, MIP-1β, PDGF, RANTES, TNF-α, and VEGF) in plasma of over 200 patients with all stages of melanoma (stage I thought IV), melanoma in situ, atypical nevi (possible pre-malignant lesions) as well as normal controls (patients with benign nevi). Due to the volume of data (27 assays for over 200 subjects), principal component analysis (PCA) was used to identify patterns (groupings) of cytokine data based on clinical subject classifications. The results suggested that the most significant differences in plasma cytokine levels among the different patient diagnostic categories was detected in the category of patients with stage IV melanoma/metastatic melanoma (circled brown spheres in FIG. 3). Closer analysis of the data indicated that the most significant difference among the cytokines was noted for IL-4 (FIG. 4, left), the key regulatory cytokine of the Th2 immune response. Statistical comparisons (Student's t-test) of the mean cytokine concentrations between patients with metastatic melanoma (stage IV) versus all others depicted a pattern of predominance of other Th2 cytokines in addition to IL-4 (IL-10, IL-13, IL-5, eotaxin, IL-9) in patients with stage IV melanoma (FIG. 4, right). For all of these cytokines, the pattern of plasma concentrations across stages of melanoma was similar to that of IL-4 (no significant changes among any of the patient cohorts except stage IV melanoma). These results are complementary to reports suggesting an increased frequency of Th2 cells in the blood of patients with advanced cancer (as well as chronic infections) relative to normal controls (Inagaki et al., *Int. J. Cancer*, 118(12):3054-61 (2006); Matsuda et al., *Dis. Colon Rectum*, 49(4):507-16 (2006); Agarwal et al., *Cancer Immunol. Immunother.*, 55(6):734-43 (2006); and Kumar et al., *Oncol. Rep.*, 15(6):1513-6 (2006)).

Preliminary analysis of three random samples from patients with stage IV melanoma also demonstrated an increased frequency of Th2 cells. These data support the hypothesis of the presence of a state of Th2 mediated chronic inflammation in patients with metastatic melanoma and offer an explanation to the observed state of systemic immune dysfunction (e.g., inability to generate effective immunity following vaccination with cancer vaccines) emulating other clinical conditions characterized by Th2 driven systemic chronic inflammation.

PBMC isolated from patients with benign nevi, atypical (including dysplastic) nevi, as well as patients with in situ, stage I, II, III or IV melanoma were analyzed by flow cytometry to determine the frequencies of T, NK, and dendritic (DC) cell subsets. There were not significant differences in frequencies of T-cell among stages of melanoma as determined by numbers of CD3, CD4 or CD8 positive T-cells (Table 2). Similarly, no significant differences were found in activated T-cells (CD3/CD69), total NK cells (CD16/56$^+$, CD3$^-$), or most DC subset parameters. As patients with stage IV melanoma appeared to differ significantly from all others with regard to plasma cytokine profiles, the cell subset analysis of patients with stage IV melanoma were compared relative to all others. The analysis revealed no significant differences among most parameters (Table 3) with the following exceptions: (a) the frequency of naïve T-cells (CD3/CD62L$^+$) as well as activated DC (CD11c/CD83$^+$) were significantly less in patients with stage IV melanoma; and (b) the frequency of tetramer positive CTL for gp100 and tyrosinase (but not MART-1 or CMV and EBV) were increased in patients with stage IV melanoma. Due to lack of available biospecimens, $T_{h1}$ and $T_{h2}$ enumeration could not be performed. These data suggested that there appeared to be some level of "immune activation" in patients with metastatic melanoma that was different from all other cohorts, and this was consistent with a state of $T_{h2}$ mediated "chronic inflammation."

TABLE 2

Square root averages of cell subsets with the 95% confidence interval (parenthesis). The p-value represents the comparison across all stages of disease.

| Variable | Benign (N = 22) | Atypical (N = 21) | In-Situ (N = 27) | Stage I (N = 27) | Stage II (N = 12) | Stage III (N = 13) | Stage IV (N = 32) | p-value |
|---|---|---|---|---|---|---|---|---|
| Sqrt CD3 | 4.78 (4.20, 5.37) | 5.46 (4.88, 6.04) | 5.74 (5.23, 6.25) | 5.29 (4.78, 5.80) | 5.50 (4.79, 6.20) | 5.63 (4.94, 6.32) | 4.94 (3.92, 5.96) | 0.20 |

TABLE 2-continued

Square root averages of cell subsets with the 95% confidence interval
(parenthesis). The p-value represents the comparison across all stages of disease.

| Variable | Benign (N = 22) | Atypical (N = 21) | In-Situ (N = 27) | Stage I (N = 27) | Stage II (N = 12) | Stage III (N = 13) | Stage IV (N = 32) | p-value |
|---|---|---|---|---|---|---|---|---|
| Sqrt CD3/4 | 3.97 (3.41, 4.53) | 4.54 (3.98, 5.09) | 4.57 (4.08, 5.06) | 4.40 (3.91, 4.89) | 4.51 (3.84, 5.19) | 4.64 (3.98, 5.31) | 4.00 (3.02, 4.97) | 0.59 |
| Sqrt CD3/8 | 2.43 (1.96, 2.89) | 2.82 (2.36, 3.28) | 3.17 (2.77, 3.57) | 2.64 (2.23, 3.04) | 2.60 (2.04, 3.16) | 2.93 (2.39, 3.48) | 2.56 (1.76, 3.37) | 0.20 |
| Sqrt CD3/62L | 2.92 (2.23, 3.60) | 2.77 (2.09, 3.45) | 2.91 (2.31, 3.50) | 2.28 (1.69, 2.88) | 2.67 (1.84, 3.49) | 3.15 (2.35, 3.96) | 1.13 (0.00, 2.32) | 0.17 |
| Sqrt CD3/69 | 0.40 (0.18, 0.61) | 0.54 (0.32, 0.75) | 0.56 (0.37, 0.75) | 0.50 (0.31, 0.69) | 0.50 (0.24, 0.76) | 0.48 (0.23, 0.74) | 0.49 (0.12, 0.87) | 0.95 |
| Sqrt CD3/16+56 | 3.03 (2.62, 3.44) | 3.54 (3.13, 3.95) | 3.44 (3.08, 3.80) | 3.30 (2.94, 3.66) | 3.18 (2.68, 3.68) | 3.43 (2.95, 3.92) | 3.48 (2.77, 4.20) | 0.55 |
| Sqrt 11c+/14− | 1.88 (1.59, 2.17) | 2.15 (1.86, 2.44) | 1.89 (1.64, 2.14) | 1.89 (1.64, 2.15) | 2.00 (1.65, 2.35) | 1.98 (1.64, 2.32) | 1.64 (1.13, 2.14) | 0.66 |
| Sqrt 11c+/14+ | 2.74 (2.18, 3.3) | 3.07 (2.52, 3.63) | 2.60 (2.11, 3.09) | 3.11 (2.62, 3.60) | 2.86 (2.18, 3.54) | 3.50 (2.84, 4.16) | 2.80 (1.82, 3.77) | 0.33 |
| Sqrt 11c+/DR | 0.80 (0.65, 0.95) | 0.91 (0.77, 1.06) | 0.74 (0.61, 0.87) | 0.87 (0.74, 1.00) | 0.74 (0.56, 0.92) | 0.86 (0.69, 1.03) | 0.78 (0.53, 1.03) | 0.48 |
| Sqrt 11c+/DR+ | 1.06 (0.88, 1.23) | 1.21 (1.04, 1.39) | 1.06 (0.90, 1.21) | 1.05 (0.90, 1.20) | 1.11 (0.90, 1.32) | 1.01 (0.81, 1.22) | 1.33 (1.03, 1.64) | 0.45 |
| Sqrt 11c/80 | 0.22 (0.17, 0.26) | 0.26 (0.21, 0.30) | 0.24 (0.20, 0.28) | 0.24 (0.20, 0.28) | 0.21 (0.15, 0.26) | 0.25 (0.20, 0.31) | 0.18 (0.10, 0.25) | 0.46 |
| Sqrt 11c/83 | 0.21 (0.15, 0.28) | 0.27 (0.21, 0.33) | 0.24 (0.19, 0.30) | 0.24 (0.18, 0.29) | 0.18 (0.11, 0.26) | 0.19 (0.12, 0.26) | 0.1 (0.00, 0.21) | 0.18 |
| Sqrt 11c/86 | 0.70 (0.56, 0.83) | 0.82 (0.68, 0.95) | 0.71 (0.59, 0.82) | 0.76 (0.64, 0.87) | 0.70 (0.53, 0.86) | 0.75 (0.59, 0.91) | 0.74 (0.50, 0.97) | 0.84 |
| Sqrt DR/40 | 0.54 (0.37, 0.70) | 0.74 (0.58, 0.91) | 0.55 (0.40, 0.69) | 0.62 (0.47, 0.76) | 0.60 (0.40, 0.80) | 0.61 (0.42, 0.80) | 0.82 (0.54, 1.11) | 0.36 |

TABLE 3

| Cytokine | p-value (stage IV vs all other) |
|---|---|
| IL-4 | $1.73 \times 10^{-12}$ |
| RANTES (CCL5) | $6.17 \times 10^{-06}$ |
| IL-10 | $5.29 \times 10^{-05}$ |
| Eotaxin (CCL11) | $8.31 \times 10^{-05}$ |
| IP-10 (CXCL10) | 0.0007 |
| IL-13 | 0.002 |
| IL-12p70 | 0.005 |
| IL-7, IL-9 | 0.009 |
| VEGF, MIB-1b (CCL4) | 0.02 |
| GM-CSF | 0.03 |
| IL-5 | 0.05 |
| IL-15, TNFa, MIP-1a, FGF, IL-2, G-CSF, IL-8, IL-6, IFN-g, MCP-1, IL-17, PDGF, IL-1ra, IL-1b | >0.05 |

Figure 5A:
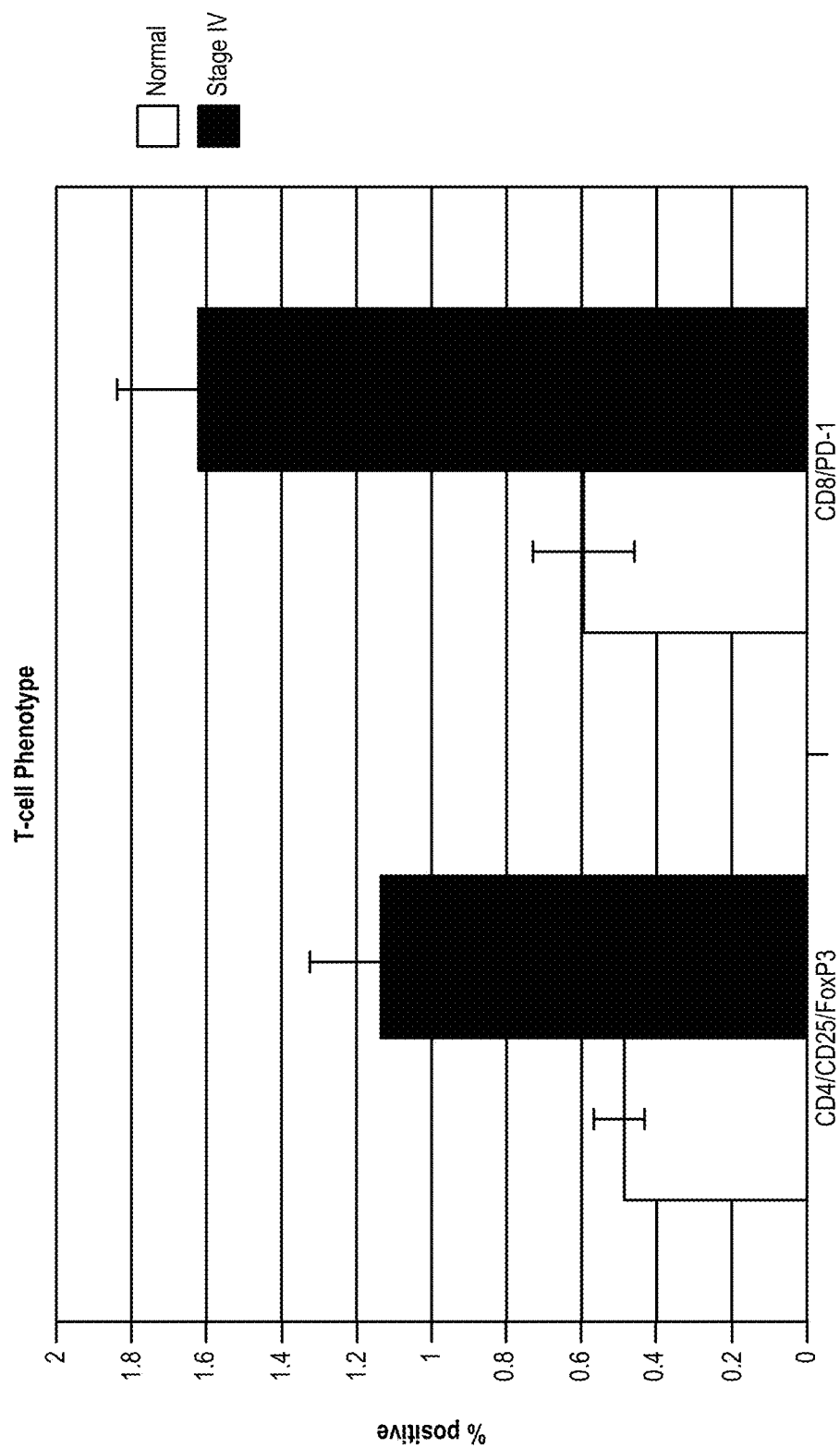
FIG. 5: Assessment of T-cell phenotype and function in healthy donors and stage IV melanoma patients. The number of T-cells exhibiting the FoxP3 (Treg) or PD-1 phenotype in peripheral blood was determined in healthy donors and stage IV melanoma patients (A). The frequency of FoxP3 positive cells were measured by 3-color flow cytometry, CD4-PC5, CD25-PE and FoxP3-Alexa flour 488. The mean percent (+/−SD) of FoxP3 positive were determined from the CD4 and CD25 double positive population. The mean frequency (+/−SD) of PD-1+ cells was measured from the CD8+ population. The frequency (+/−SD) of tetramer positive (CMV or MART-1) CD8+ T cells was compared among normal volunteers and patients with stage IV melanoma (B).
Figure 5B:
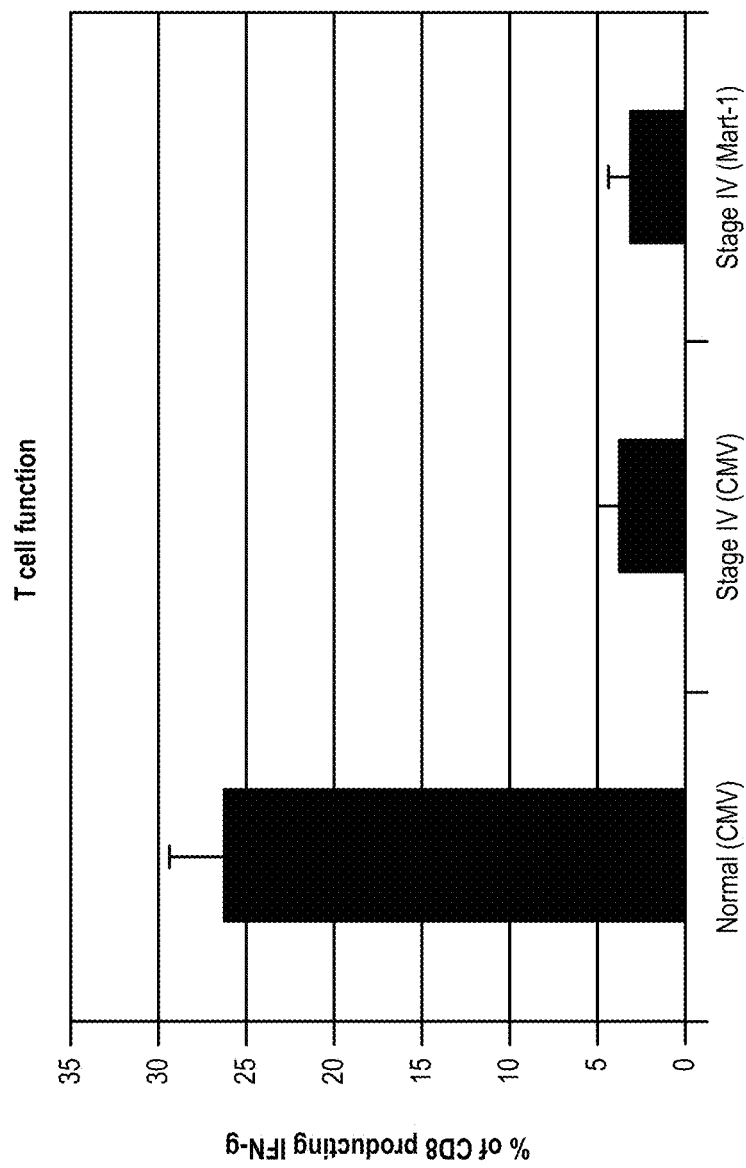

The emerging data seemed to suggest that patients with stage IV melanoma, unlike all other patients with earlier stages of melanoma (or healthy controls), existed in a state of systemic $T_{h2}$ dominance with some evidence of cellular immune activation in peripheral blood (increased frequencies of tumor specific CTL and decreased frequencies of naïve T cells). This immune homeostasis profile resembled a state of $T_{h2}$ dominant "chronic inflammation," similar to chronic viral infection (Sester et al., *Am. J. Transplant*, 5(6):1483-89 (2005)). A reflection of the chronic inflammatory state of chronic viral infection as well as metastatic melanoma is an increase in peripheral blood PD-1+ (exhausted) T-cells (Wong et al., *Int. Immunol.*, 19:1223-34 (2007)). The same was found to be true in the patient cohort of stage IV melanoma patients compared to healthy controls (FIG. 5a). This was further supported by functional assessment of antigen specific CTL, revealing a significant reduction in the frequency of functional recall antigen ($CMV_{495-503}$) specific CTL in patients with stage IV melanoma versus healthy volunteers (FIG. 5b). Less than 5% of tumor antigen specific, PBMC derived, tetramer positive CTL (MART-1) were capable of intracellular IFN-γ synthesis suggesting immune tolerance.

Example 4

Figure 6A:
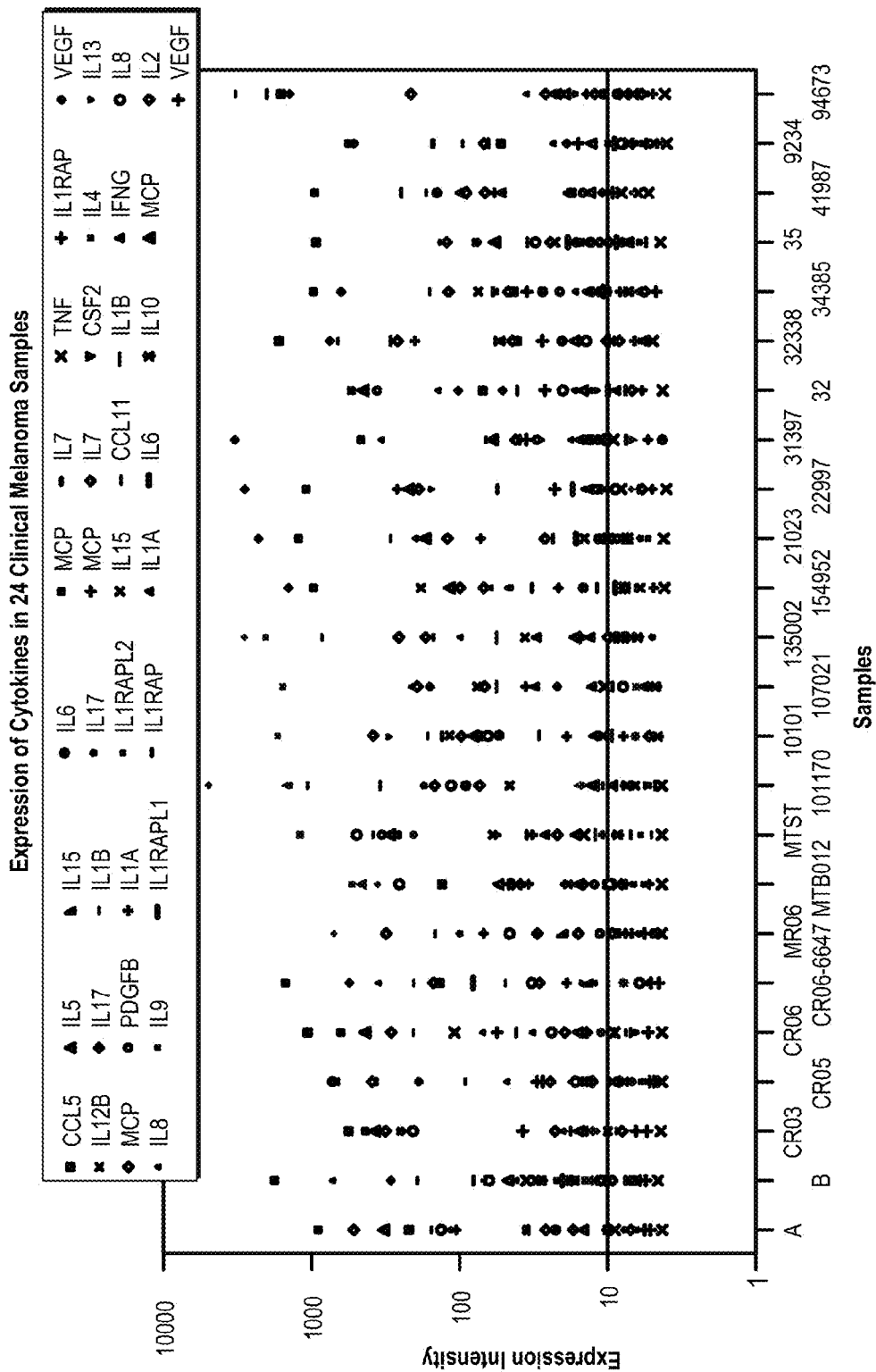
FIG. 6: VEGF levels in patients with metastatic melanoma. (A) RNA expression of cytokines in human metastatic melanoma tissue. Twenty-four frozen biopsies of metastatic melanoma tumor tissues was used to extract RNA for expression array analysis. Illustrated are the RNA expression intensity profiles of 45 probes for 24 cytokines. (B) Comparison of expression intensities between genes coding for Th1 (IFN-γ and IL-2), Th2 (IL-4, IL-5, IL-10, and IL-13) cytokines and VEGF. There were no statistically significant differences when comparing Th1 vs. Th2 cytokine expression levels (p=0.04). There was a statistically significant difference when comparing VEGF expression with Th1 or Th2 cytokines (p<0.001). Levels of significance were determined using the Wilcoxin signed-rank test. (C) ELISA (mean concentration+/−SD) for VEGF-A was performed on plasma samples from healthy donors (n=30) and stage IV melanoma patients (n=40).
Figure 6B:
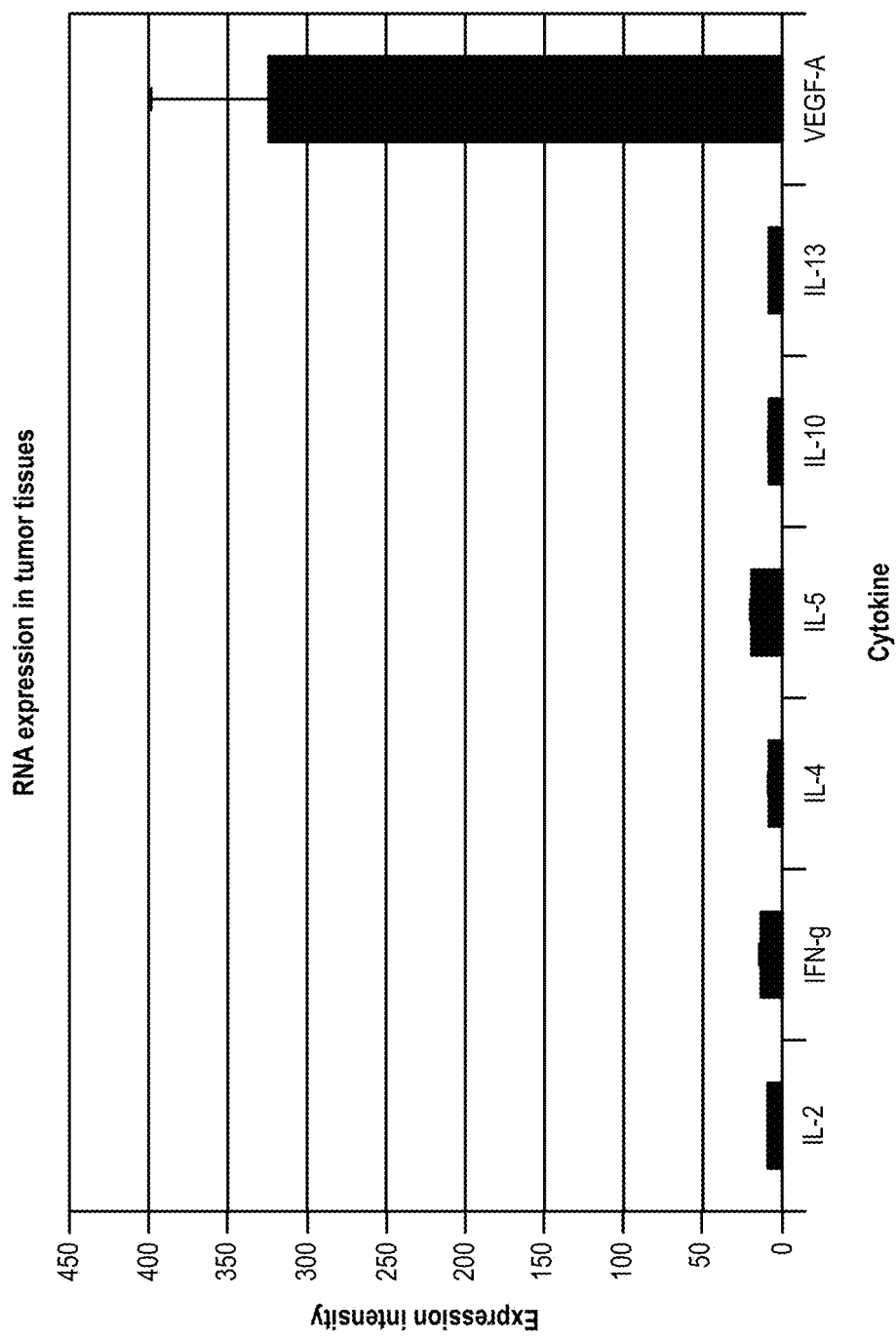
Figure 6C:
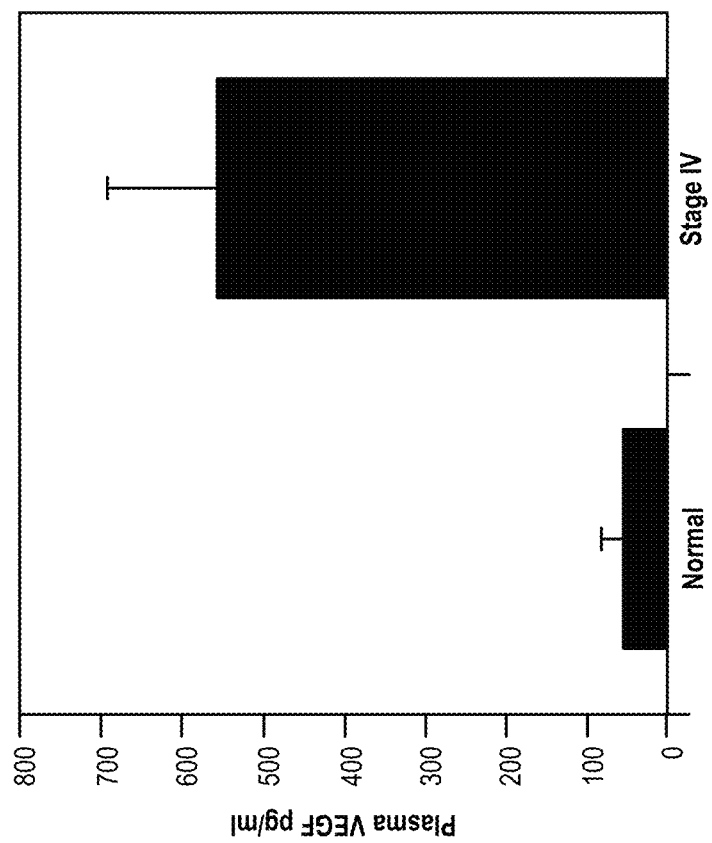

Role of Malignant Melanoma Cells in Tumor-Associated $Th_2$/IL-4 Mediated Systemic Chronic Inflammation The plasma cytokine profiling data comparing patients across all stages of melanoma suggested that the greatest differences in the measured parameters occurred in the setting of metastatic melanoma (stage 4 disease). Therefore, it was hypothesized, that the presence of visible metastatic disease was in some way responsible for the detected $Th_2$ cytokine dominance in these patients and was likely the result of molecules produced by the tumor and/or its interaction with surrounding immune cells. To that end, the mRNA expression profile of 24 biopsy specimens of human metastatic melanoma was analyzed looking for up-regulation of expression of known regulatory molecules of immunity (cytokines and chemokines). The mRNA was extracted from frozen sections in areas that by H&E staining appeared to contain pure tumor tissue (devoid of necrotic tissue, stroma or lymphocytic infiltrates). The RNA was analyzed using an Affymetrix U133 plus 2.0 array. In this experiment, concurrent blood samples were not available from the patients for whom tumor tissues existed. The expression of 23 cytokines (45 probes): IL1a and b, IL-1ra, IL-2, IL-4, IL-5, IL-6, IL-7, IL-8, IL-9, IL-10, IL-12, IL-13, IL-15, IL-17, IFN-γ, CCL5, CCL11, CSF-2, MCP-1, TNF-α, VEGF was analyzed. The objective of the experiment was to determine whether or not the malignancy itself was the source of $T_{h2}$ cytokines that were detected in plasma. The data revealed that many of the probed cytokines, chemokines, and growth factors are up-regulated in tumor tissue (FIG. 6a). However, there were no differences in expression of $T_{h1}$ vs. $T_{h2}$ cytokines (IFN-γ vs. IL-4, IL-5, IL-10, and IL-13, FIG. 6b) in tumor tissues suggesting that the observed $T_{h2}$ cytokine predominance in plasma was not derived from the tumor. However, of the tested cytokines, the most highly/frequently up-regulated transcript in the tumor samples was VEGF (FIG. 6b). Plasma VEGF levels were significantly higher in metastatic melanoma patients relative to healthy donors, (FIG. 6c), consistent with published reports (Tas et al., *Melanoma Res.*, 16:405-11 (2006)). Considering the described immune modulatory (down-regulatory) properties of VEGF (Gabrilovich et al., *Nat. Med.*, 2:1096-103 (1996)), it was postulated that tumor derived VEGF could be responsible for the $T_{h2}$ polarization in patients with stage IV melanoma (away from the normal state of $T_{h1}$ dominance).

Figure 7:
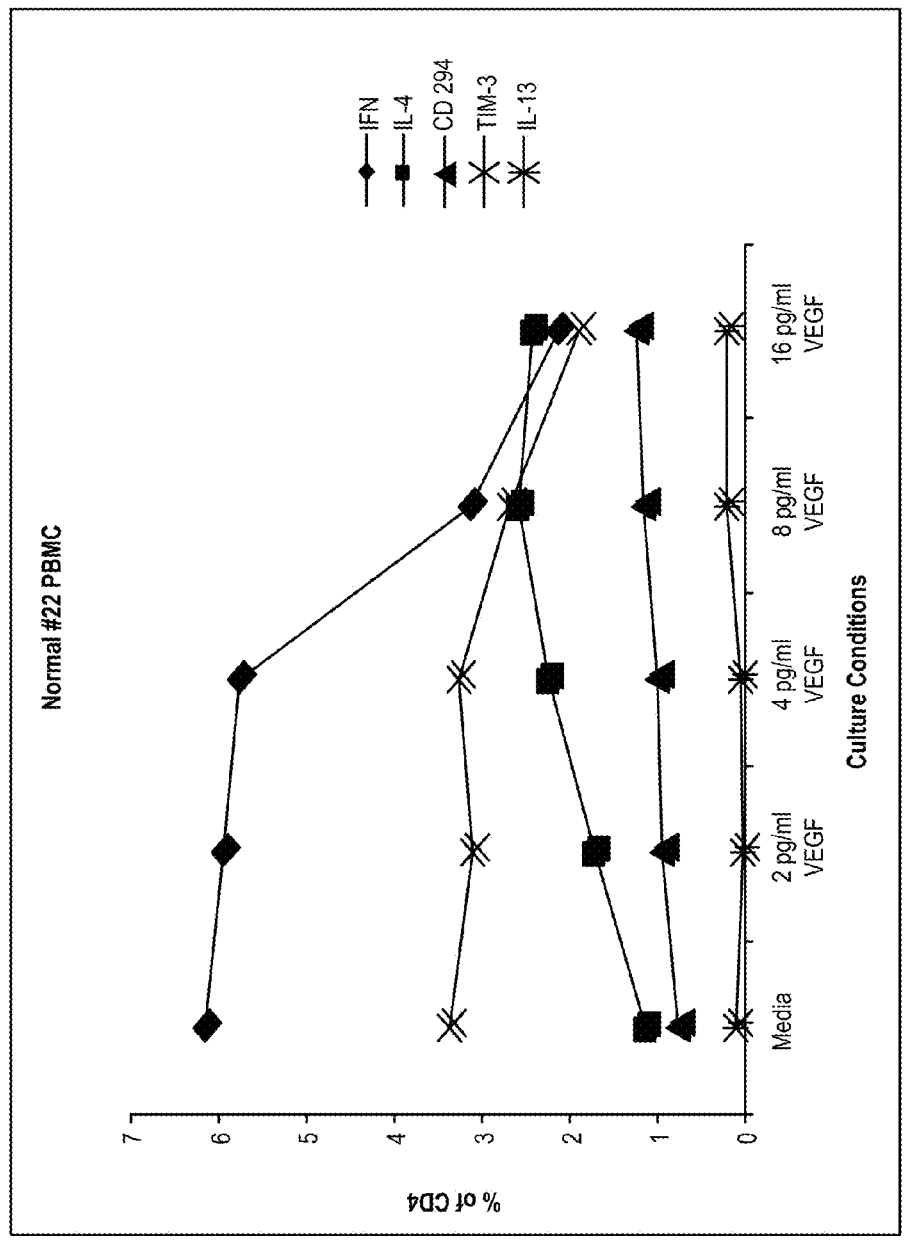
FIG. 7. Healthy donor PBMCs were cultured in vitro for 48 hours in the presence of increasing concentrations of recombinant human VEGFA. At the end of the incubation, cells were stimulated with PMA and ionomycin, in the presence of brefeldin A and stained for intracellular IFNγ, IL-4, or IL-13 and surface immunophenotyped for CD294 or TIM-3. Cells were then analyzed for the frequency of CD4 cells (% of CD4) expressing said phenotypes using flow cytometry.

VEGF has been associated with DC polarization towards $DC_2$ leading to $Th_2$ immune responses (e.g., asthma). Likewise, $Th_2$ cytokines (e.g., IL-4, IL-5, and IL-13) have been associated with increased production of VEGF by a range of different cell types including smooth muscle cells. Preliminary data demonstrated that the addition of recombinant human VEGFA to a 2-day culture of normal blood-donor derived PBMC appeared to shift Th polarity away from $Th_1$ and towards $Th_2$ in a dose dependent fashion (FIG. 7). The addition of VEGF to the cell culture favored a reduction of Th cells capable of IFNγ synthesis and TIM-3 expression ($Th_1$) and increased the frequency of Th cells capable of IL-4 synthesis and CD294 surface expression ($Th_2$). The effect on intracellular IL13 production was less pronounced. Thus, it appeared that VEGFA had a direct impact on human PBMC $Th_1/Th_2$ polarization in vitro.

Figure 8A:
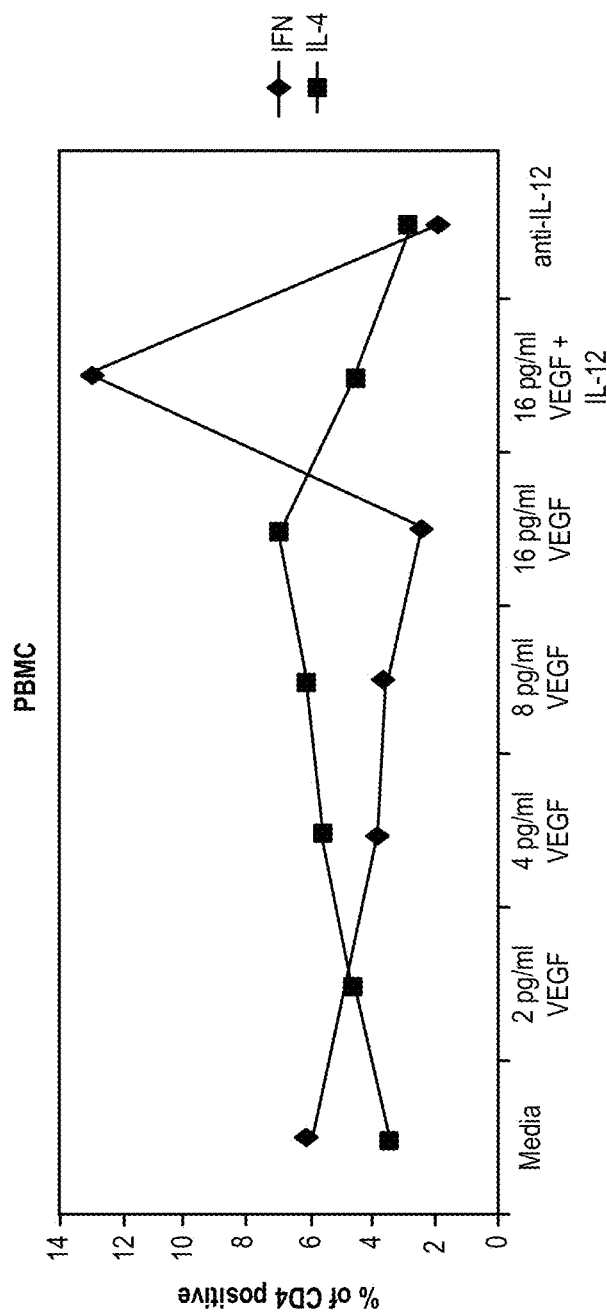
FIG. 8: Co-culture with recombinant human VEGF shifts T-helper polarity from Th1 (IFN-γ) to Th2 (IL-4) predominance. PBMC (A) isolated from healthy donors were stimulated with PMA and ionomycin in the presence of brefeldin-A, permeabolized, and intracellularly stained for human IFN-γ (FITC) and human IL-4 (PE). PBMC were exposed to increasing concentrations of VEGF (0-16 pg/mL) without/with IL-12. All cells were immunostained with PC5 anti-human CD4. Purified CD4+ T-cells (B) were negatively isolated using Miltenyi beads, cultured, and stained in the same fashion as PBMC (A). Similar results were observed in 5 different experiments.
Figure 8B:
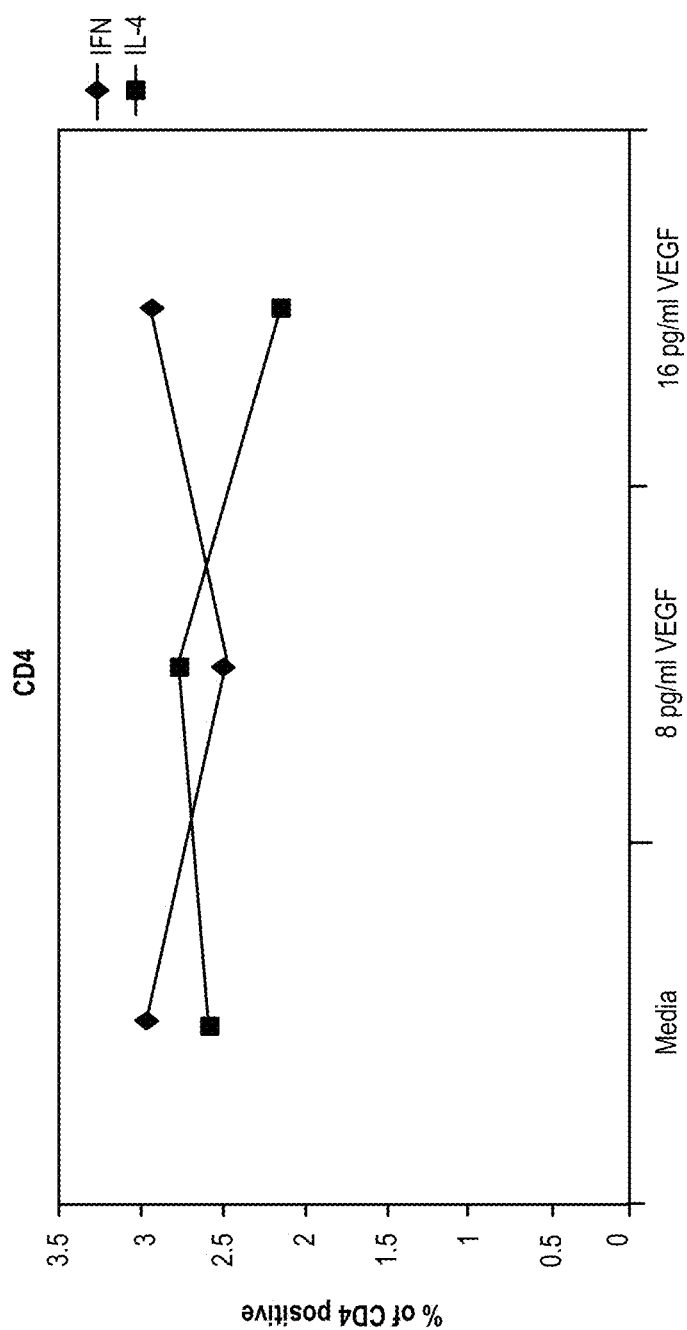

In addition, healthy donor PBMC were stimulated with $CD3^+/CD28^+$ expander micro-beads for 3 days with increasing concentrations (1 pg/mL-16 pg/mL) of recombinant VEGF and assessed intracellular cytokine production of IL-4 ($T_{h2}$ cytokine) and IFN-γ ($T_{h1}$ cytokine) in $CD4^+$ T-cells at the end of in vitro culture (FIG. 8a). The data demonstrated that increasing concentrations of VEGF resulted in a dose-dependent reversal of the relative ratio of $T_{h1}$ to $T_{h2}$ cells in favor of $T_{h2}$. Increased concentrations of VEGF were associated with a decrease in the number of $T_{h1}$ cells ($CD4^+/IFNγ^+$) with an associated reciprocal increase in $T_{h2}$ cells ($CD4^+/IL-4^+$). The polarizing effects of VEGF were lost if the assay was performed with purified CD4 cells only (FIG. 8b) suggesting that the observed $T_h$ polarization effect of VEGF is indirect, likely mediated by other PBMC. The addition of 10 μg/mL of IL-12 to the culture containing 16 pg/mL of VEGF prevented the shift in T-helper polarity from $T_{h1}$ to $T_{h2}$; addition of anti-human IL-12 antibody to the stimulated PBMC mimicked the effect of VEGF (FIG. 8a). These data suggest a possible role for monocyte/macrophages in the PBMC preparation as the mediators of the VEGF induced $T_h$ polarization.

Figure 9:
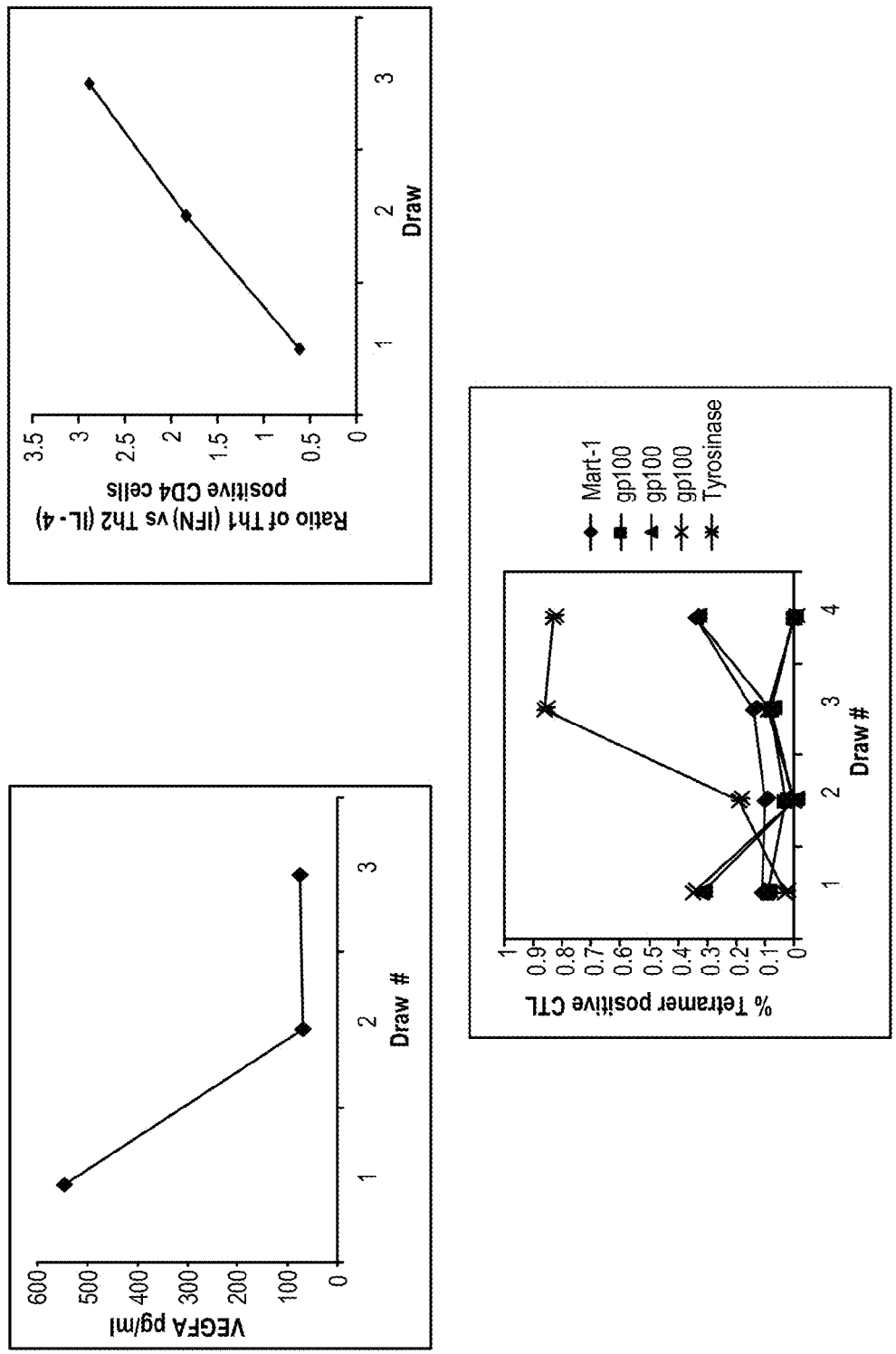
FIG. 9. Changes in plasma VEGF levels (plasma VEGFA in pg/mL; top left) at three time points in a single patient with metastatic melanoma treated on protocol N047a correlate with improved Th1/Th2 ratio as determined by intracellular staining of CD4+ cells for IFN gamma or IL-4 (top right). These also correlate with emergence of increased frequencies of tumor specific CTL (bottom right) as determined by tetramer assay.

To gain further insight into the potential role of tumor produced VEGF on systemic immune homeostasis in vivo in humans with metastatic melanoma, frozen peripheral blood specimens were randomly selected from a recently completed clinical trial (N047a) where patients with metastatic melanoma were treated with chemotherapy (paclitaxel+carboplatin) and a specific anti-VEGFA antibody (bevacizumab). They were analyzed for changes in plasma VEGFA levels and $Th_1/Th_2$ polarity as well as frequency of tumor specific CTL (tetramer assay). If VEGF was responsible for $Th_2$ polarization, its suppression using chemotherapy/anti-VEGF therapy would revert the $Th_1/Th_2$ balance back to normal (normal ratio is 1:1) and perhaps result in emergence of naturally processed anti-tumor specific CTL. Also, this particular clinical trial was chosen because of: (1) available, appropriately stored biospecimens; and (2) this single arm phase II clinical trial yielded favorable clinical outcomes for patients with metastatic melanoma, suggesting possible clinical relevance of this therapeutic strategy. As illustrated in this example from a single patient (FIG. 9), coincident with the decrease of plasma VEGFA concentrations (as a result of therapy, FIG. 9, top left), there was an increase in $Th_1:Th_2$ ratio away from $Th_2$ and towards $Th_1$ (FIG. 9, top right) at the same time as the increase in frequency of tumor specific CTL in peripheral blood (reactive against melanoma differentiation antigens: MART-1, gp100 or tyrosinase, FIG. 9, bottom right). Similar observations were made in two other patient samples. In all three cases, the increases in tumor specific CTL tetramer frequency coincided with a reduction in plasma VEGFA levels to normal levels and a shift in Th polarity away from $Th_2$ and towards $Th_1$. Of note, such an increase in CTL frequency was not observed when analyzing the same immunological parameters from patients with metastatic melanoma treated with chemotherapy alone (nab-paclitaxel+carboplatin) without the anti-VEGF antibody (three patients analyzed from protocol N057e). Of note, the presented data were consistent with a published anecdotal observation from a prior clinical trials demonstrating increase in tumor specific CTL tetramer frequency coincident with reduction of plasma VEGFC levels in patients with metastatic melanoma treated with a thrombospondin-1 analog, ABT-510 (Markovic et al., *Am. J. Clin. Oncol.*, 30(3):303-9 (2007)). Therefore, viewed in the context of the current hypothesis, in addition to the originally postulated anti-tumor and anti-angiogenic goals of paclitaxel/carboplatin/bevacizumab therapy, the effect of chemotherapy (paclitaxel and carboplatin) may also have depleted (lymphodepleted) the pre-existing state of "chronic inflammation"; and the VEGF inhibitor (bevacizumab) may have allowed reconstitution of tumor-specific immunity in a $Th_1$ (not $Th_2$) dominant systemic environment. Thus, it is possible that the additional, unanticipated, immunomodulatory effect of this therapy may have added to the observed therapeutic clinical result. Repeated treatments with lymphodepleting chemotherapy may have also inadvertently lead to ultimate depletion of the beneficial anti-tumor immune response as well, allowing tumor progression. Perhaps, this explains in part the clinical outcomes of protocol N047a demonstrating a dramatic improvement in median progression free survival (from 6 weeks to 6 months) with a not nearly as significant an improvement in overall survival (from 8 months to 12 months).

Figure 10:
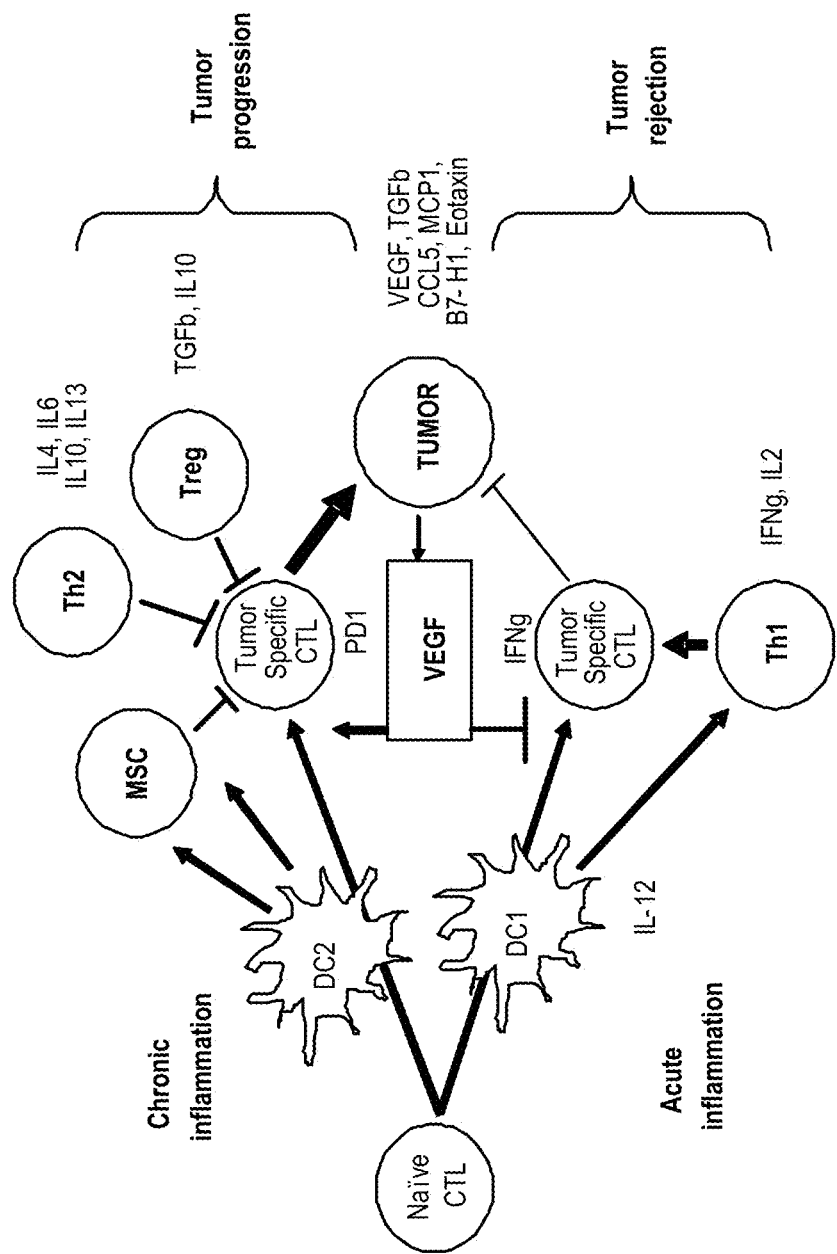
FIG. 10. Cellular interactions of acute and chronic inflammation. MSC (myeloid suppressor cell); Th1 & Th2 (T helper lymphocytes type 1 & 2); Treg: regulatory T cell; DC1 (dendritic cells, type 1); DC2 (dendritic cells type 2); CTL (cytotoxic T lymphocyte); illustrated is central role of tumor derived VEGF in polarizing immunity towards Th2 mediated "chronic inflammation".

In summary, preliminary data suggests that patients with advanced (metastatic) melanoma exhibit systemic features of $Th_2$-mediated chronic inflammation that appears at least in part mediated by tumor-secreted VEGF (FIG. 10). This state of chronic inflammation effectively dampens spontaneously developed anti-tumor CTL immune responses and significantly reduces the efficacy of de novo immunization efforts with cancer vaccines/immune modulation in this patient population. Evidence exists that the observed $Th_2$/VEGF pathway could be self sustaining and exists in both physiologic (pregnancy) as well as other pathologic states (e.g., asthma) in humans. Disruption of the $Th_2$ driven systemic chronic inflammation in patients with advanced melanoma (and possibly other malignancies) and reconstitution of effective immunity ($Th_1$ dominance) could potentially translate into effective therapy with clinically meaningful results. Therefore, an improved understanding of this mechanism of tumor mediated immune dysfunction/tumor progression as a function of $Th_2$-mediated chronic inflammation could yield therapeutic targets for cancer therapy with agents already in clinical development for $Th_2$ mediated disorders (e.g., anti-IL-4 antibody).

Example 5

Confirm the Mechanism of Tumor-Induced (VEGF Mediated), $Th_2$ Driven Chronic Inflammation Across Stages of Melanoma Focusing on the Functional State of Cellular Anti-Tumor Immunity The identified cytokine profiles of plasma suggests the existence of a $Th_2$ dominant systemic immune environment in the blood of patients with metastatic melanoma. The analysis of the cellular/functional counterpart of the immune response in these patients across all stages of melanoma remains unknown. To confirm the hypothesis of $Th_2$ dominant systemic immunity, the existence of reciprocal, $Th_2$ polarized, changes in the cellular immune response in these patients across stages of melanoma that will correlate with the described changes in plasma cytokine and VEGF concentrations is determined. To address this, one can (a) enumerate $Th_1$, $Th_2$ and $T_{reg}$ cells across stages of melanoma; (b); analyze the numbers and functional/differentiation state of circulating DC ($DC_1/DC_2$) across stages of melanoma ($DC_2$ driven $Th_2$ polarization) and (c) analyze the functional status (active vs. tolerant) of both tumor-specific (e.g. MART-1, gp100, tyrosinase) and recall antigen specific (EBV, CMV) CTL in the HLA-A2$^+$ subset of patients, across stages of melanoma. These data can be combined with the existing data on plasma cytokine levels and correlated looking for patterns of $Th_1$ vs. $Th_2$ cytokine/cellular profiles across patients and in relation to plasma VEGF levels.

Enumeration of $Th_1$, $Th_2$ and $T_{reg}$ Cells Across Stages of Melanoma.

In order to assess whether the $Th_2$ cytokine predominance in plasma of patients with metastatic melanoma is truly a reflection of a systemic immune polarization towards $Th_2$ driven chronic inflammation, one can ascertain the expected corresponding changes in the frequencies of circulating Th cell subsets across disease stage using frozen PMBC samples corresponding to plasma cytokine samples described above. The available frozen PBMC can be thawed and analyzed for the relative numbers of $Th_1$, $Th_2$ and $T_{reg}$. CD4 cells can be isolated from thawed PBMC specimens using paramagnetic beads coated with anti-CD4 (Dynal, Oslo, Norway), and they can be incubated with mouse-anti-human CD3/CD28 coated "stimulator" micro-beads (R and D Systems Minneapolis, Minn.) for 6 hours in the presence of 1 ug/ml brefeldin A, (Sigma Aldrich, St Louis, Mo.). After stimulation, the cells can be fixed, permeablized, and stained with APC conjugated mouse anti-human CD4 (Becton Dickinson, San Jose, Calif.) and FITC conjugated mouse anti-human IFNγ and anti-IL-13 (R and D Systems Minneapolis, Minn.). The stained samples can be analyzed by flow cytometry (FACScan™ (a flow cytometer) and Cellquest™ software (Becton-Dickinson, San Jose, Calif.). The results can indicate the percentage of IFNγ positive/IL-13 (or IL-4) negative ($Th_1$) and IFNγ negative/IL-13 (or IL-4) positive ($Th_2$) helper T cells.

Figure 11:
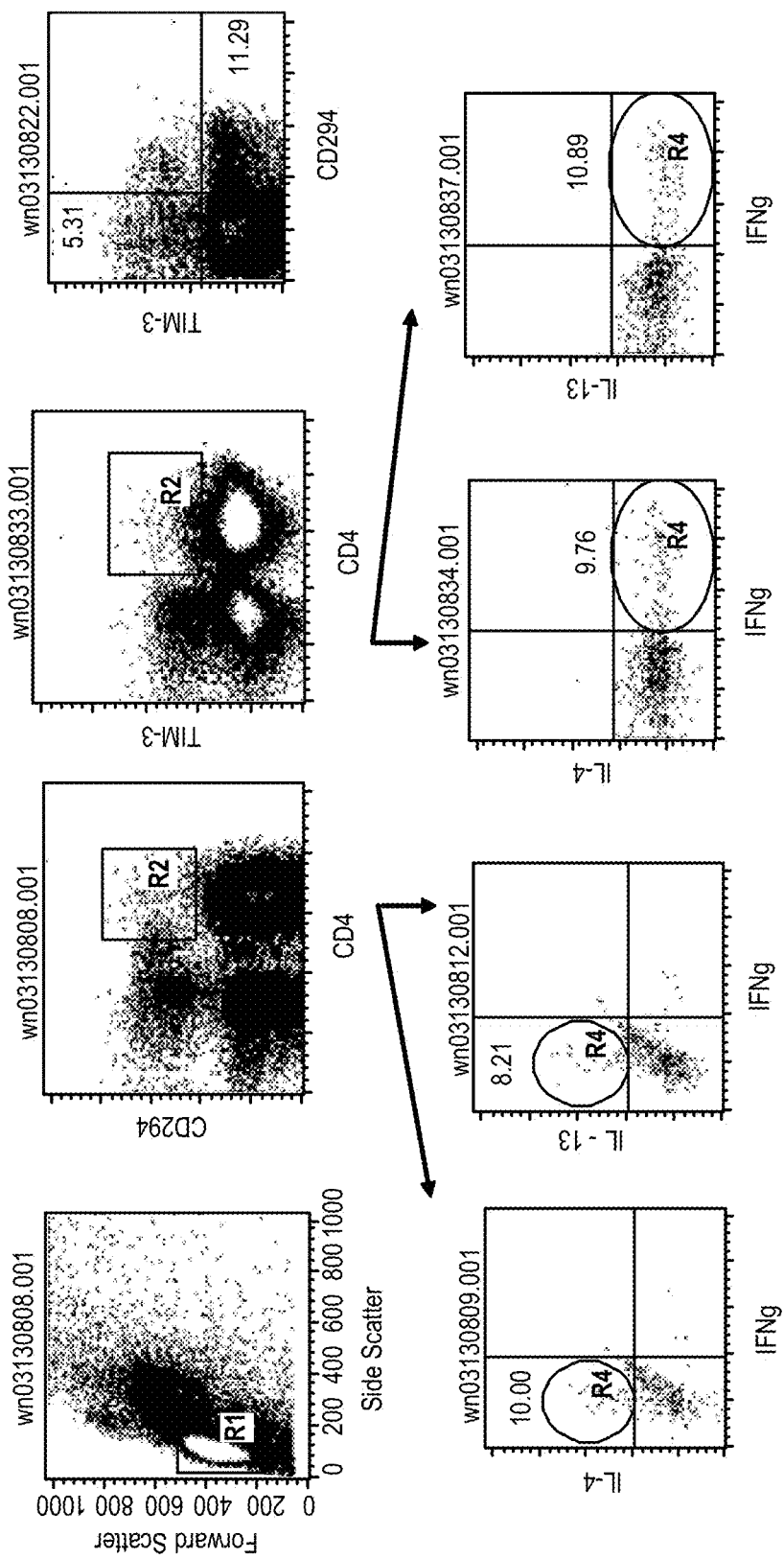
FIG. 11: Correlation of surface immunophenotyping for CD294 and TIM-3 with intracellular IL-4, IL-13 and IFNγ for the purposes of enumeration of Th2 and Th1 cells respectively.

GLP validation of anti-CD294 and anti-TIM-3 cell-surface immunostaining can be completed for the distinction of $Th_2$ vs. $Th_1$ cells in ex vivo (unstimulated) frozen PBMC, respectively. Preliminary data suggested that CD4/CD294 positive $Th_2$ cells exclusively produce IL-4 and IL-13 and not IFNγ upon CD3/CD28 stimulation. Conversely, CD4/TIM-3 positive $Th_1$ cells exclusively produced IFNγ and not IL-4 and IL-13 following the same in vitro stimulation (FIG. 11). Once validated, the assay can be standardized and applied to the battery of tests described herein.

Enumeration of $T_{reg}$ can be performed using intracellular staining for FoxP3 of CD4/25 positive lymphocytes. Immunophenotyping can be conducted using commercially available monoclonal antibodies (Biolegend; San Diego, Calif.). Samples can be analyzed by flow-cytometry by FACScan® and data processed using Cellquest® software (Becton-Dickinson, Franklin Lakes, N.J.).

Assessment of Peripheral Blood DC Subset ($DC_1/DC_2$) and Activation/Differentiation Status.

In order to ascertain whether or not the state of $Th_2$ driven systemic chronic inflammation is primarily a function of systemic DC polarization towards $DC_2$ (from $DC_1$) leading to HTL polarization from $Th_1$ to $Th_2$ in patients with advanced melanoma, one can quantify the relative numbers and functional states of $DC_1$ and $DC_2$ in patients with melanoma across stages of disease. These data can be analyzed in conjunction with corresponding plasma cytokine/VEGF and Th subset data (above). Therefore, the available, frozen PBMC corresponding to the plasma cytokine samples described above can be thawed and analyzed for the relative numbers of DC subsets defined by expression of CD11c$^+$/CD123– ($DC_1$), and CD11c–/CD123$^+$ ($DC_2$). Each subset can be analyzed for surface expression of co-stimulatory molecules (CD80, 83, 86). Immunophenotyping can be conducted using commercially available monoclonal antibodies (BD Pharmingen; San Jose, Calif.). Samples can be analyzed by flow-cytometry by FACScan® and data processed using Cellquest® software (Becton-Dickinson, Franklin Lakes, N.J.).

Analysis of the Functional Status (Active/Tolerant) of Tumor Specific (MART-1, gp100, Tyrosinase) and Recall Antigen Specific (EBV, CMV) CTL in the HLA-A2$^+$ Subset of Patients Across Stages of Melanoma.

Available frozen PBMC for the same cell repository as described herein can be analyzed for the frequency and functional capacity (exhausted, tolerant vs. non-tolerant subsets) of tumor specific and recall antigen specific CTL. If the hypothesis of tumor mediated, $Th_2$-driven chronic inflammation is correct, the predominant phenotype of the tumor (and recall) antigen specific CTL can be one of tolerance (inability to synthesize intracellular IFNγ upon congnant stimulation with tumor-specific peptides) and exhaustion (expression of PD-1). The latter has already been suggested to be true (Rosenberg et al., *J. Immunol.*, 175(9):6169-76 (2005)). Immunophenotyping of PBMC can be performed using tetramers for melanoma differentiation antigen specific, HLA-A2 congnant peptides (MART-1$_{27-35}$, gp100$_{209-217}$ and tyrosinase$_{368-376}$) as well as A2 cognant peptides of EBV and CMV (Beckman Coulter, San Diego, Calif.). For tetramer analysis, thawed PBMC can be stained with FITC conjugated anti-CD8, PC5 conjugated anti-human CD4, CD14 and CD19, and conjugated HLA-A2 tetramers containing peptides from CMV, EBV (controls), MART-1$_{27-35}$, gp100$_{209-217}$ and tyrosinase$_{368-376}$. Samples can be analyzed by flow-cytometry and data processed using Cellquest® software (Becton-Dickinson, Franklin Lakes, N.J.). Gates can be set on lymphocytes that were CD4, CD14, and CD19 (PC5) negative and CD8 (APC) positive. Ongoing quality assurance (QA) data suggests an inter-assay variability with a coefficient of variation (CV) below 5%. Standard control samples can be run alongside all experiments. If the standard control samples generate results beyond ±2SD of the mean, all assay results can be rejected and the experiment repeated.

Functional analysis of tetramer positive CTL can be performed in patient samples demonstrating tetramer frequencies of at least 0.1% to melanoma differentiation or recall antigens. One can proceed to ascertain the ability of tetramer positive CTL to synthesize interferon-γ (IFNγ) upon stimulation with cognate peptide presented in the context of HLA-A2 and anti-CD28 co-stimulation using artificial antigen presenting cell (aAPC) stimulation. The details of this method are described elsewhere (Markovic et al., *Clin. Exp. Immunol.*, 145(3):438-47 (2006)). In brief, previously frozen patient PBMC can be thawed in batches, labeled with PE conjugated tetramers (Beckman Coulter, San Diego, Calif.), and stimulated for 6 hours, in the presence of 1 μg/mL brefeldin A, (Sigma Aldrich, St Louis, Mo.) with pararamagnetic beads (Dynal, Oslo, Norway) coated with peptide loaded HLA-A2 (Beckman Coulter San Diego, Calif.) and mouse anti-human CD28 (R and D Systems Minneapolis, Minn.). After stimulation, the cells can be fixed, permeablized, and stained with APC conjugated mouse anti-human CD8 (Becton Dickinson, San Jose, Calif.) and FITC conjugated mouse anti-human IFN-gamma (R and D Systems Minneapolis, Minn.). The stained samples can be analyzed by flow cytometry (FACScan™ and Cellquest™ software (Becton-Dickinson, San Jose, Calif.). The results can indicate the percentage of tetramer positive CTL able vs. unable to synthesize intracellular IFNγ. Ongoing QA data suggests an inter-assay variability with a CV of below 9%. Standard control samples can be run alongside all experiments. If the standard control samples generate results beyond ±25D of the mean, all assay results can be rejected, and the experiment repeated.

Laboratory Data Summary and Statistical Analysis.

All blood samples were registered, collected, processed and annotated. Sample break down per diagnostic category is described in Table 4.

immune parameters with a primary focus on $Th_1/Th_2$ balance and functional tumor specific CTL immunity. The trials are listed in the Table 5. The patients enrolled into these trials had a blood specimen collected before initiation of therapy and after one cycle of treatment. This can provide data on the immediate impact of therapy on our VEGF/Th2/immune parameters of interest.

TABLE 5

Summary of available biospecimens from therapeutic clinical trials for stage IV melanoma

| Study number | Treatment regimen | Number of patients enrolled (accrual as of May 1, 2008) |
|---|---|---|
| N0377 | RAD001[2] | 53 (completed) |
| N047a | Paclitaxel + Carboplatin + Bevacizumab[1] | 53 (completed) |
| N057e | Abraxane + Carboplatin | 74 (completed) |
| MC057f | Temozolomide | 86 (12) |
|  | Paclitaxel + Carboplatin | 86 (0) |
| N0675 | RAD001[2] + Temozolomide | 43 (6) |
| N0775 | Abraxane + Carboplatin + Bevacizumab[1] | 43 (0) |
|  | Temozolomide + Bevacizumab | 43 (0) |

[1] Humanized anti-VEGFA antibody;
[2] rapamycin analog, inhibitor of mTOR (down-regulation of VEGF synthesis)

For each individual patient, the biospecimens collected before initiation of therapy and after one cycle of treatment can be used. This can provide data on the immediate impact of therapy on VEGF/Th2/immune parameters of interest. Additional testing for later time-points can be pursued only if justified by the initial analysis suggesting beneficial changes

TABLE 4

Summary of available biospecimens (frozen PBMC and plasma)

| | Clinical diagnostic category | | | | | | |
|---|---|---|---|---|---|---|---|
| | Benign nevi | Atypical nevi | In Situ melanoma | Stage I melanoma | Stage II melanoma | Stage III melanoma | Stage IV melanoma |
| Available frozen PBMC with already available corresponding plasma cytokine data Additional available frozen PBMC and frozen plasma as of May 1, 2008 | 26 | 16 | 35 | 36 | 12 | 16 | 30 |
| Therapeutic clinical trials | 0 | 0 | 0 | 0 | 0 | 44 | 198 |
| Melanoma blood and tissue bank (MC997g) | 10 | 0 | 22 | 43 | 38 | 209 | 421 |

Example 6

Assess the Impact of Systemic Therapeutics on the Hypothesized Tumor-Driven $Th_2$ Mediated State of Systemic Chronic Inflammation with Special Emphasis on the Role of VEGF The effects of melanoma-specific therapeutic interventions on the VEGF/$Th_2$ state of tumor-induced chronic inflammation can be examined using peripheral blood biospecimens from patients with stage IV malignant melanoma enrolled on ongoing or completed clinical trials for changes in a range of in the studied immune parameters. This can allow one to gain insight into the effects of a broad range of clinical interventions on immune homeostasis using an available (but limited) resource of biospecimens and only pursue further analysis if justified by the generated data.

Laboratory analyses of the stored PBMC can include the same assays described above and can also include: (a) PBMC immunophenotyping for immune cell subset analysis; and (b) plasma cytokine profiling.

PBMC Immunophenotyping for Immune Cell Subset Analysis.

Pre and post-treatment frozen PBMC biospecimens can be analyzed for the "global" impact of therapy on immune cell subsets. One can analyze the relative numbers of T, B, NK cells, monocytes and DC, and their activation status using commercially available monoclonal antibodies directed at the following antigens: CD3, CD4, CD8, CD11c, CD14, C16, CD19, CD20, CD25, CD45RA/RO, CD56, CD69, CD63L, CD80, CD83, CD86, CD123, DR, foxP3 (BD Pharmingen; San Jose, Calif.). Immunophenotyping can be performed using manufacturer's instruction in batch samples of the same patients analyzed on the same day. The stained samples can be analyzed by flow cytometry (FACScan™ and Cellquest™ software (Becton-Dickinson, San Jose, Calif.). PBMC isolated from patients prior to B7-DC XAb and 15 days after antibody treatment can be assayed. Changes in the numbers of cells bearing the lymphocyte markers in pared comparisons for patients prior to B7-DC XAb treatment can be used to ascertain antibody treatment effects.

Plasma Cytokine Profiling.

In order to complement the PBMC derived cellular immunity analyses, one can add plasma cytokine measurements in the same samples (paired PBMC and plasma testing). To that end, one can profile the serum cytokine changes as a result of specific therapy for all available specimens before and after treatment. The BioRad human 27-plex cytokine panel can be used (Cat #171-A11127, Bio-Rad, San Diego Calif.) for the measurements of plasma concentrations of IL-1$\beta$, IL-1r$\alpha$, IL-2, IL-4, IL-5, IL-6, IL-7, IL-8, IL-9, IL-10, IL-12(p70), IL-13, IL-15, IL-17, basic FGF, Eotaxin, G-CSF, GM-CSF, IFN-$\gamma$, IP-10, MCP-1, MIP-1$\alpha$, MIP-1$\beta$, PDGF, RANTES, TNF-$\alpha$, and VEGF. The assay can be performed as per the manufacturer's directions. Briefly, 100 µL of Bio-Plex assay buffer can be added to each well of a MultiScreen MABVN 1.2 µm microfiltration plate followed by the addition of 50 µL of the multiplex bead preparation. Following washing of the beads with the addition of 100 µL of wash buffer, 50 µL the samples or the standards can be added to each well and incubated with shaking for 30 minutes at room temperature. The plasma (1:3 dilution) and standards can be diluted using the Bio-Plex human serum diluent kit and plated in duplicate. Standard curves can be generated with a mixture of 27 cytokine standards and eight serial dilutions ranging from 0-32,000 pg/mL. The plate can then be washed 3 times followed by incubation of each well in 25 µL of pre-mixed detection antibodies for 30 minutes with shaking. The plate can further be washed and 50 µL of streptavidin solution were added to each well and incubated for 10 minutes at room temperature with shaking. The beads can be given a final washing and resuspension in 125 µL of Bio-Plex assay buffer. Cytokine levels in the sera can be quantified by analyzing 100 µL of each well on a Bio-Plex using Bio-Plex Manager software version 4.0. Normal values for plasma cytokine concentrations were generated by analyzing 30 plasma samples from healthy donors (blood donors at the Mayo Clinic Dept. of Transfusion Medicine). A set of five normal plasma samples (standards) can be run along side all batches of plasma analysis. If the cytokine concentrations of the "standard" samples differ by more than 20%, results can be rejected, and the plasma samples re-analyzed.

Example 7

Prospectively Follow Changes of Immune Homeostasis (Evolution of Systemic Chronic Inflammation) in High-Risk Patients after Complete Resection of Advanced Melanoma Until Subsequent Tumor Relapse To better understand the clinical relevance of these differences in immune homeostasis and study the kinetics of their evolution in humans as they develop clinically detectable metastatic cancer (melanoma), one can perform a prospective clinical trial in which patients with surgically resected metastatic melanoma (and in a state of chronic inflammation) undergo complete resection of their tumors as part of their clinical care and are subsequently followed at regular time-intervals until tumor relapse. It is hypothesize that following surgical resection, the state of systemic "chronic inflammation" will resolve. These patients can then be followed at regular intervals (every 2 months), and their blood analyzed for emergence of $Th_2$-mediated chronic inflammation, until clinical tumor relapse/recurrence of metastatic melanoma (approximately 50% of patients will relapse within 18 months of surgery). This study will depict the time-sequence and thresholds of systemic changes in immune homeostasis (chronic inflammation) as they evolve towards the development of relapsed metastatic melanoma. Sufficient blood specimens (100 mL every 2 months) can be collected to allow complete analysis as well as provide some additional material for further testing (if necessary). The clinical trial can be powered based on the inter-patient variability of the most prominent immune abnormality in patients with metastatic melanoma (e.g. variability of plasma IL-4 concentrations) determined herein. If successful, these data can clinically validate the changes in immune homeostasis as they impact the natural history of metastatic melanoma and describe potential targets for future therapy. Additionally, as all patients on this study will undergo surgical resection of metastatic melanoma as well as undergo concurrent comprehensive immunological testing, their surgical tissues can be processed and preserved for analysis addressing the influence of the tumor on the observed immunological profile (multiple frozen blocks for future immunohistochemical study and mRNA extraction). All tumor tissue can undergo genomic mRNA expression profiling as well as IHC analysis for infiltrating immune cell subsets (funded under separate, existing instruments). These data can correlate the relationship of immunity in the tumor microenvironment with that of systemic immunity in metastatic cancer.

Study Design.

The clinical trail can be conducted in the context of the clinical trials program of the Melanoma Study Group of the Mayo Clinic Cancer Center. All patients with the diagnosis of metastatic melanoma that are planned to undergo complete surgical resection of their malignancy can be offered participation in this study. The objective of the study can be to profile the changes in immune homeostasis from pre-surgery, post-surgery and all through the time of clinically detectable tumor relapse. It is hypothesized that the state of VEGF/$Th_2$ driven chronic inflammation can be established pre-surgery, resolved soon after surgery and slowly re-develop in the months prior to clinical tumor relapse.

For the purposes of this study, patients can be clinically followed in accordance to clinical practice (every 2 months). Patients can be asked to donate 100 mL of blood at each follow-up time point. The blood can be collected, processed, and stored in accordance to existing procedures for immunological testing. Immune homeostasis analysis can be conducted in batches to limit inter-assay variability. Specific focus/priority can be given to parameters reflecting $Th_1$/$Th_2$ balance, frequency of functional/tolerant tumor (or recall) antigen specific CTL as well as plasma cytokine and VEGF levels. At the time of clinical relapse, patients can be re-tested, and the tumor biopsied for histologic confirmation. Available tumor tissues can be analyzed for expression of tumor associated antigens (immunohistochemistry for MART-1, gp100 and tyrosinase) as well as tumor infiltrating lymphocytes and compared to the original surgical specimen for each individual patient. In the rare events where patients can undergo another curative surgical resection at the time of relapse, they may continue on study following the outlined follow-up/testing schedule until such a time when a tumor relapse is no longer surgically resectable. See, e.g., Table 6.

Eligibility Criteria.

Required Characteristics/Inclusion Criteria:
1. HLA-A2+ adult patients (age≥18 years) with metastatic malignant melanoma who are planned to undergo complete resection for metastatic disease as part of their regular medical care.
2. The following laboratory values obtained ≤14 days prior to registration: hemoglobin≥9.0 g/dL; platelet count≥75,000/μL; and AST≤3×ULN.
3. Ability to provide informed consent.
4. Willingness to return to clinic for follow-up.
5. ECOG performance status 0, 1 or 2.
6. Willingness to participate in the mandatory translational research component of the study.

Contraindications/Exclusion Criteria:
1. Uncontrolled or current infection.
2. Known standard therapy for the patient's disease that is potentially curative or proven capable of extending life expectancy.
3. Any of the following prior therapies with interval since most recent treatment: (a) chemotherapy ≤4 weeks prior to registration; or (b) biologic therapy ≤4 weeks prior to registration.
4. Any of the following as this regimen may be harmful to a developing fetus or nursing child: (a) pregnant women; (b) nursing women; or (c) women of childbearing potential or their sexual partners who are unwilling to employ adequate contraception (condoms, diaphragm, birth control pills, injections, intrauterine device (IUD), surgical sterilization, subcutaneous implants, or abstinence, etc).
5. Known immune deficiency or ongoing immunosuppressive therapy.

TABLE 6

Test schedule

| Tests and procedures | ≤14 days prior to registration | <7 days prior to scheduled surgery | Every 2 months after surgery until surgically unresectable relapse[2] | At time of tumor relapse[2] |
|---|---|---|---|---|
| History and exam, weight, performance status | X | | X | X |
| Vital signs | X | | X | |
| Disease evaluation (clinical/imaging) | X | | X | X |
| Hematology group WBC, ALC, ANC, Hgb, platelets | X | | X | X |
| Chemistry group AST, LDH, Alk Phos, Creat, K, Na, LDH | X | | X | X |
| Immunology studies | | $X^R$ | $X^R$ | $X^R$ |
| HLA typing | $X^R$, | | | |
| Tumor typing for MART1, gp 100 and tyrosinase; profile of infiltrating lymphocytes | $X^R$ | | | $X^R$ |
| Serum pregnancy test[1] | $X^R$ | | | |

[1]Only for women of child-bearing age;
[2]if a patient has a melanoma relapse that is surgically completely resectable, they may continue on study with the same follow-up/testing schedule until relapse is no longer surgically resectable;
[R]research funded Example 8

TGFβ Alters Th1/Th2 Ratios

Figure 12:
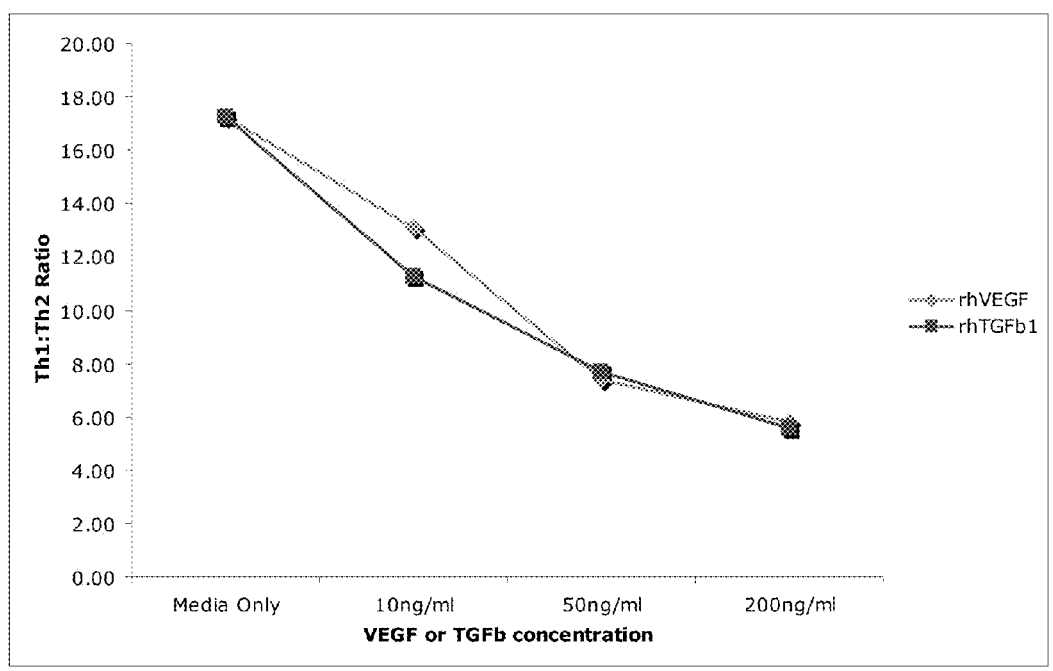
FIG. 12: Changes in the ratio of human PBMC derived CD4 T cell subsets (Th1 vs. Th2) following in vitro incubation with varying concentrations of VEGFA or TGFβ. These results indicate that both VEGFA and TGFβ have a similar effect on Th1/Th2 polarity in human PBMC derived CD4 cells.

CD4 T cells (Th1 and Th2 CD4 T cells) derived from human PBMC were incubated in vitro with varying concentrations of VEGFA (rhVEGFA; 10 ng/mL, 50 ng/mL, and 200 ng/mL) or TGFβ (rhTGFβ; 10 ng/mL, 50 ng/mL, and 200 ng/mL). After six hours of incubation at 37° C., the ratio of Th1 vs. Th2 (Th1/Th2) was determined. Both VEGFA and TGFβ exhibited a similar effect on Th1/Th2 polarity in human PBMC derived CD4 cells (FIG. 12).

Figure 13:
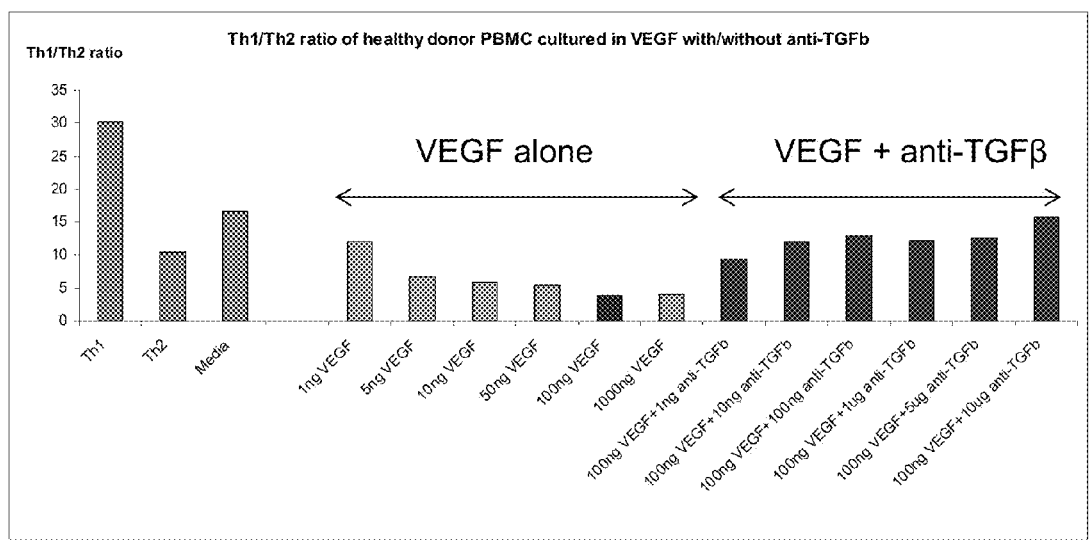
FIG. 13: Relative ratios of human PBMC derived CD4 T cells subsets (Th1 vs. Th2) cultured in vitro with varying concentrations of VEGFA in the absence or presence of increasing concentrations of anti-TGFβ neutralizing antibody. Untreated (media) as well as Th1 (Th1) and Th2 (Th2) favorable in vitro conditions are presented as controls. These results indicate that presence of anti-TGFβ antibodies reverses the Th1/Th2 modulation of VEGFA in vitro, suggesting that the observed VEGF effect in these cells may be TGFβ mediated.

CD4 T cells (Th1 and Th2 CD4 T cells) derived from human PBMC were incubated in vitro with VEGFA alone (1 ng/mL, 5 ng/mL, 10 ng/mL, 100 ng/mL, or 1000 ng/mL) or VEGFA (100 ng/mL) plus an anti-TGFβ antibody (1 ng/mL, 10 ng/mL, 100 ng/mL, 1 μg/mL, 5 μg/mL, or 10 μg/mL). The anti-TGFβ antibody was obtained from Genzyme Corp. (Cambridge, Mass.). Untreated cells (media only) as well as cells exposed to Th1 or Th2 favorable in vitro conditions were used as controls. After six hours of incubation at 37° C., the ratio of Th1 vs. Th2 (Th1/Th2) was determined. The presence of anti-TGFβ antibodies reversed the Th1/Th2 modulation of VEGFA in vitro, suggesting that the observed VEGF effect in these cells may be TGFβ mediated (FIG. 13).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A method for treating a mammal having stage IV melanoma, said method comprising:
    (a) administering to said mammal an anti-chronic inflammation treatment,
    (b) detecting, in a blood sample obtained from said mammal, a reduction in IL-4, IL-5, IL-10, and IL-13 level following said step (a), wherein said reduction is indicative of reduced global chronic inflammation, and
    (c) after detecting said reduced global chronic inflammation, administering to said mammal a cancer treatment agent under conditions wherein the presence of said melanoma is reduced, wherein said cancer treatment agent is paclitaxel, carboplatin, bevacizumab, anti-CTLA-4, a MART-1 cancer vaccine, a gp 100 cancer vaccine, a survivin cancer vaccine, or a tyrosinase cancer vaccine.
2. The method of claim 1, wherein said mammal is a human.
3. The method of claim 1, wherein said anti-chronic inflammation treatment comprises chemotherapy, radiation, an anti-IL-4 agent, an anti-IL-13 agent, or a steroid treatment.
4. The method of claim 1, wherein said cancer treatment agent is a cancer vaccine.
5. The method of claim 1, wherein said cancer vaccine is a Melan-A (MART-1), gp100, or survivin cancer vaccine.
6. The method of claim 1, wherein the period of time between the last administration of said anti-chronic inflammation treatment and the first administration of said cancer treatment agent is between two weeks and six months.

* * * * *